(12) United States Patent
Puder et al.

(10) Patent No.: US 12,337,027 B2
(45) Date of Patent: Jun. 24, 2025

(54) METHODS AND COMPOSITIONS RELATING TO LUNG REPAIR

(71) Applicant: THE CHILDREN'S MEDICAL CENTER CORPORATION, Boston, MA (US)

(72) Inventors: Mark Puder, Medfield, MA (US); Duy T. Dao, Boston, MA (US)

(73) Assignee: THE CHILDREN'S MEDICAL CENTER CORPORATION, Boston, MA (US)

( * ) Notice: Subject to any disclaimer, the term of this patent is extended or adjusted under 35 U.S.C. 154(b) by 0 days.

(21) Appl. No.: 16/977,854

(22) PCT Filed: Jan. 24, 2019

(86) PCT No.: PCT/US2019/014867
§ 371 (c)(1),
(2) Date: Sep. 3, 2020

(87) PCT Pub. No.: WO2019/182683
PCT Pub. Date: Sep. 26, 2019

(65) Prior Publication Data
US 2021/0015899 A1    Jan. 21, 2021

Related U.S. Application Data

(60) Provisional application No. 62/646,493, filed on Mar. 22, 2018.

(51) Int. Cl.
| | | |
|---|---|---|
| *A61K 38/18* | (2006.01) | |
| *A61K 9/00* | (2006.01) | |
| *A61K 31/437* | (2006.01) | |
| *A61K 31/472* | (2006.01) | |
| *A61K 31/506* | (2006.01) | |
| *A61K 31/513* | (2006.01) | |
| *A61K 38/17* | (2006.01) | |
| *A61P 11/00* | (2006.01) | |

(52) U.S. Cl.
CPC .......... *A61K 38/179* (2013.01); *A61K 9/0014* (2013.01); *A61K 9/0019* (2013.01); *A61K 31/437* (2013.01); *A61K 31/472* (2013.01); *A61K 31/506* (2013.01); *A61K 31/513* (2013.01); *A61K 38/177* (2013.01); *A61P 11/00* (2018.01)

(58) Field of Classification Search
CPC .. A61K 38/179; A61K 9/0014; A61K 9/0019; A61K 31/437; A61K 31/472; A61K 31/506; A61K 31/513; A61K 38/177; A61P 11/00
See application file for complete search history.

(56) References Cited

U.S. PATENT DOCUMENTS

| | | | |
|---|---|---|---|
| 5,712,380 A | 1/1998 | Kendall et al. | |
| 2006/0205645 A1* | 9/2006 | Compernolle | A61K 38/1709 |
| | | | 435/7.1 |

FOREIGN PATENT DOCUMENTS

| | | | | |
|---|---|---|---|---|
| CN | 1402733 A | 3/2003 | | |
| CN | 101664409 A | 3/2010 | | |
| CN | 107683143 A | 2/2018 | | |
| WO | 2002086497 A2 | 10/2002 | | |
| WO | WO-2005034929 A2 * | 4/2005 | ............ | A61K 31/00 |
| WO | 2007009071 A2 | 1/2007 | | |
| WO | WO-2015095757 A1 * | 6/2015 | ............ | A61K 31/00 |
| WO | 2016164579 A1 | 10/2016 | | |
| WO | WO-2017143131 A1 * | 8/2017 | ........... | A61K 31/197 |

OTHER PUBLICATIONS

GSK1278863 structure, Chemspider, accessed Nov. 2, 2021 at URL chemspider.com/Chemical-Structure.33427356.html?rid=ea8a5c69-f51b-42dc-8c21-84f45ac78068. (Year: 2021).*
MK-8617 structure, Chemspider, accessed Nov. 2, 2021 at URL chemspider.com/Chemical-Structure.28424192.html?rid=1a259314-f1cc-4a32-b129-5f9164983068 (Year: 2021).*
Cygulska et al., "Roxadustat: another drug that causes pulmonary hypertension? Report of first human case," Polish archives of internal medicine 129:344-345 (2019) (Year: 2019).*
Hirota, "HIF-α Prolyl Hydroxylase Inhibitors and Their Implications for Biomedicine: A Comprehensive Review," Biomedicines 9(468) pp. 1-25 (2021) (Year: 2021).*
Nizet et al., "Interdependence of hypoxic and innate immune responses," Nature reviews immunology 9: 609-617 (2009) (Year: 2009).*
Weidemann et al., "Biology of HIF-1α," Cell death and differentiation 15:61-627 (2008) (Year: 2008).*
Gerber et al. "Differential transcriptional regulation of the two vascular endothelial growth factor receptor genes: Flt-1, but not Flk-1/KDR, is up-regulated by hypoxia." Journal of Biological Chemistry 272(38): 23659-23667 (1997).
Gerber et al. "VEGF is required for growth and survival in neonatal mice." Development 126(6): 1149-1159 (1999).
Lahm et al. "The Critical Role of Vascular Endothelial Growth Factor in Pulmonary Vascular Remodeling After Lung Injury." Shock 28(1):4-14 (2007).
Perkins et al. "Regulation of vascular endothelial growth factor bioactivity in patients with acute lung injury." Thorax 60(2): 153-158 (2005).
Tang et al. "Excess soluble vascular endothelial growth factor receptor-1 in amnionic fluid impairs lung growth in rats: linking preeclampsia with bronchopulmonary dysplasia." American Journal of Physiology—Lung Cellular and Molecular Physiology 302(1): 36-46 (2011).

(Continued)

*Primary Examiner* — Julie Ha
*Assistant Examiner* — Kristina M Hellman
(74) *Attorney, Agent, or Firm* — Nixon Peabody LLP; David S. Resnick; Nicole D. Kling

(57) ABSTRACT

Described herein are methods of inducing and/or enhancing lung growth and/or repair by administering an agonist of sFlt1-Hif signaling to a subject or contacting lung tissue with an agonist of sFlt1-Hif signaling.

32 Claims, 16 Drawing Sheets

Specification includes a Sequence Listing.

(56) References Cited

OTHER PUBLICATIONS

Tuder et al. "Vascular endothelial growth factor of the lung: friend or foe." Current Opinion in Pharmacology 8(3):255-260 (2008).
Asikainen et al. "Stimulation of HIF-1α, HIF-2α, and VEGF by prolyl 4-hydroxylase inhibition in human lung endothelial and epithelial cells." Free Radical Biology and Medicine 38(8): 1002-1013 (2005).
Asikainen et al. "Activation of hypoxia-inducible factors in hyperoxia through prolyl 4-hydroxylase blockade in cells and explants of primate lung." Proceedings of the National Academy of Sciences 102.29 (2005): 10212-10217.
Asikainen et al. "Improved lung growth and function through hypoxia-inducible factor in primate chronic lung disease of prematurity" Faseb J., 20(10): 1698-700 (2006).
Ad hoc Statement Committee. "Mechanisms and Limits of Induced Postnatal Lung Growth" Am J Repir Crit Care Med 170:319-343 (2004).
Hsia et al. "Quantitative morphology of compensatory lung growth." Eur Respir Rev 15:148-156 (2006).
Paisley et al. "The pneumonectomy model of compensatory lung growth: Insights into lung regeneration." Pharmacology & Therapeutics 142:196-205 (2014).
Thane et al. "Lung regeneration and translational implications of the postpneumonectomy model." Translational Research 163.4: 363-376 (2014).

* cited by examiner

Soluble Flt1

Control sFlt1

SEQUENCE LISTING

<160> NUMBER OF SEQ ID NOS: 13

<210> SEQ ID NO 1
<211> LENGTH: 6499
<212> TYPE: DNA
<213> ORGANISM: Homo sapiens

<400> SEQUENCE: 1

```
atcgaggtcc gcgggaggct cggagcgcgc caggcggaca ctcctctcgg ctcctccccg      60
gcagcggcgg cggctcggag cgggctccgg ggctcgggtg cagcggccag cgggcgcctg     120
gcggcgagga ttacccgggg aagtggttgt ctcctggctg gagccgcgag acgggcgctc     180
agggcgcggg gccggcggcg gcgaacgaga ggacggactc tggcggccgg gtcgttggcc     240
gcggggagcg cgggcaccgg gcgagcaggc cgcgtcgcgc tcaccatggt cagctactgg     300
gacaccgggg tcctgctgtg cgcgctgctc agctgtctgc ttctcacagg atctagttca     360
ggttcaaaat taaaagatcc tgaactgagt ttaaaaggca cccagcacat catgcaagca     420
```

-continued

```
ggccagacac tgcatctcca atgcaggggg gaagcagccc ataaatggtc tttgcctgaa    480
atggtgagta aggaaagcga aaggctgagc ataactaaat ctgcctgtgg aagaaatggc    540
aaacaattct gcagtacttt aaccttgaac acagctcaag caaaccacac tggcttctac    600
agctgcaaat atctagctgt acctacttca aagaagaagg aaacagaatc tgcaatctat    660
atatttatta gtgatacagg tagaccttc gtagagatgt acagtgaaat ccccgaaatt    720
atacacatga ctgaaggaag ggagctcgtc attccctgcc gggttacgtc acctaacatc    780
actgttactt taaaaaagtt tccacttgac actttgatcc ctgatggaaa acgcataatc    840
tgggacagta gaaagggctt catcatatca aatgcaacgt acaaagaaat agggcttctg    900
acctgtgaag caacagtcaa tgggcatttg tataagacaa actatctcac acatcgacaa    960
accaatacaa tcatagatgt ccaaataagc acaccacgcc cagtcaaatt acttagaggc   1020
catactcttg tcctcaattg tactgctacc actcccttga acacgagagt tcaaatgacc   1080
tggagttacc ctgatgaaaa aaataagaga gcttccgtaa ggcgacgaat tgaccaaagc   1140
aattcccatg ccaacatatt ctacagtgtt cttactattg acaaaatgca gaacaaagac   1200
aaaggacttt atacttgtcg tgtaaggagt ggaccatcat tcaaatctgt taacacctca   1260
gtgcatatat atgataaagc attcatcact gtgaaacatc gaaaacagca ggtgcttgaa   1320
accgtagctg gcaagcggtc ttaccggctc tctatgaaag tgaaggcatt ccctcgccg   1380 gaagttgtat ggtaaaaga tgggttacct gcgactgaga atctgctcg ctatttgact   1440 cgtggctact cgttaattat caaggacgta actgaagagg atgcagggaa ttatacaatc   1500
ttgctgagca taaacagtc aaatgtgttt aaaaacctca ctgccactct aattgtcaat   1560
gtgaaacccc agatttacga aaaggccgtg tcatcgtttc cagacccggc tctctaccca   1620
ctgggcagca gacaaatcct gacttgtacc gcatatggta tccctcaacc tacaatcaag   1680
tggttctggc acccctgtaa ccataatcat tccgaagcaa ggtgtgactt tgttccaat   1740 aatgaagagt cctttatcct ggatgctgac agcaacatgg aaacagaat tgagagcatc   1800 actcagcgca tggcaataat agaaggaaag aataagatgg ctagcacctt ggttgtggct   1860
gactctagaa tttctggaat ctacatttgc atagcttcca ataaagttgg gactgtggga   1920
agaaacataa gcttttatat cacagatgtg ccaaatgggt ttcatgttaa cttggaaaaa   1980
atgccgacgg aaggagagga cctgaaactg tcttgcacag ttaacaagtt cttatacaga   2040
gacgttactt ggattttact gcggacagtt aataacagaa caatgcacta cagtattagc   2100 aagcaaaaa tggccatcac taaggagcac tccatcactc ttaatcttac catcatgaat   2160
gtttccctgc aagattcagg cacctatgcc tgcagagcca ggaatgtata cacaggggaa   2220
gaaatcctcc agaagaaaga aattacaatc agaggtgagc actgcaacaa aaaggctgtt   2280
ttctctcgga tctccaaatt taaaagcaca aggaatgatt gtaccacaca agtaatgta   2340 aaacattaaa ggactcatta aaagtaaca gttgtctcat atcatcttga tttattgtca   2400
ctgttgctaa ctttcaggct cggaggagat gctcctccca aaatgagttc ggagatgata   2460
gcagtaataa tgagaccccc gggccccagc tctgggcccc ccattcaggc cgaggggct   2520 gctccggggg gccgacttgg tgcacgtttg gatttggagg atccctgcac tgccttctct   2580
gtgtttgttg ctcttgctgt tttctcctgc ctgataaaca caacttggg atgatccttt   2640 ccttccattt tgatgccaac ctcttttat ttttaagtgt tgaagctgca caaactgaat   2700
aatttaaaca aatgctggtt tctgccaaag atggacacga ataagttaat tttccagctc   2760
agaatgagta cagttgaatt tgagactctg tcggacttct gcctggtttt atttgggact   2820
```

```
atttcatctg ctcttgattt gtaaatagca cctggatagc aagttataat gcttatttat    2880
ttgaaaatgc ttttttttt tttacgttaa gcacatttat cttgaactgg agcttctaaa    2940
atgggcccca ggggtgcaag atgttggtgt aattcagaga tagtaaaggt ttatcgcagt    3000
gtgaattata agagtccatc caaatcaacg tcccctccct cctctcatgc gatccaggta    3060
attatgcagt tagtgccaca gtagactagc ctagcaaagg gtttgctcct tgctgtctct    3120
gactgcacca cacagctatt gatggcagct gaaagaaagt ggatcatgcc ttaattttaa    3180
atattcctgt cctctggtta ttattttaag gaacttcatc atgttaaaat gacagcattc    3240
aaaggtgtac cacaatcaat ttatcaagga aataaaggct attgtaacca gagatttaat    3300
gcattcttct aaatgtaaat ttaaaatttg ccctttaaaa aagtccactt tccccatatg    3360
caaatgttaa taggattttt atggggatta agaagcggca aaactacaga agcagaattc    3420
aaagtaattt aaaaaataca caccagtttt aaatcaagag aagttgtaat ctcttgtttt    3480
aagcttgcgt ttgagggaaa atgactttt caccaattta atatgcattg ttctgttgtt    3540
tttatttatg attgatcatt atatgtgact tgcataaact atttaaaaaa aaaaactata    3600
atgaccaaaa tagccatggc tgagaaacac agtggctggg cagttcaata ggaggtgaca    3660
atatgacaac ttctcaagct tgggaactca ccagactgtt tcctccttta ggtaacagat    3720
tctgtcccac ggctaaactt gtcttcacg tgggaattgc ttttgtcaaa cgtgaaagag    3780
taaacaatag catttcccca gaatgccagt tttatggagc cccaaatgct ctgaaaacaa    3840
ttagtaacct ggaagttgtc agcccaaagg aaagaaaaat caattgtatc ttgaaatttt    3900
acctatggct ctttggcctg gcttctttgt tcattataag ttagtgtgtt ccttcaggaa    3960
acaatgcctt aataccatag aacatggggg ccttaatagt tgctaacatt aaaaaagcaa    4020
acagaatgat tgagggatcc ttatgaaaac aaaatggtga attggacatg cagaacctac    4080
catttccttc ccctgtttgc aattttttgtg gggaggggag gatgttagta tttacaaaag    4140
atgattttaa gaacttccaa gagatgagtt taagaattcc atagagtatt agttgttcac    4200
tgtgtaatta atccttccgg agagtctttt ttttttttt taaagaaact ttgggtggg    4260 ttttgttttt tattagttac cctaggggta tgttaccctg gggtatgaag ggaggtgaag    4320
ataacggagg ggggagaaaa aaaaaaggag aaaaaaggag cctaaaatgg ggaataattg    4380
aaatggaaca gggggtgtga ggctggttcc tcagtcccca ttccaaacgg aggatagaag    4440
ctgtgtattt atgtgacctg gcagatctct ggggccataa cactgaaaag tgaaagaacc    4500
tggtgggcag ctatctttgg ctactgataa ccagcagaaa tgtctgttaa ttctgatttt    4560
ctcaatttga agggatcagc tacactgtta aattttggaa agccactacc tacttccatc    4620
aagtaactta ggtttcgaaa tatgggttca acgcacctcc cttattcaaa atgtcaaaat    4680
agattattat aatgtataaa gtaagaattg acaaaatatg attcttgggt tgattggtca    4740
tttagaaact agccaaaagt gagacttta atgtagaaca ttttcagaa atgggtacaa    4800 agaaaaatgc atattactgt atatttcaga gtgtttatgt gaaccttgta tttaattgag    4860
agtcccatgt acgttctgca gccttttgc tgcttctatc atctgaagtt tgtgtagtac    4920
aaataaggcc tttgggattc ttaatgacat ttatgttaaa atgttctctt ctcttttaaac    4980 accgttttcc aatccacctg tcagggagtc caaatcgtgt ctgtgttgat gatgctatac    5040
tttgtagcta gaaaaacaat tttagtgttg tgggctctgt attcagactt ccttttttaca    5100 agaccgatgg gcagtgatag attatttttat catatttaat gcatgggaaa tagtgtgctg    5160
```

| | |
|---|---|
| aggaagctat taaaagtata actcagtgaa ttgggtctga gttttaaatg agatatttca | 5220 |
| aaattggctt gccactgtaa aagcgactaa ataataatat gatactgttc tttatgatct | 5280 |
| tgtcatgttt cactgatatg tttggggtct tcactatgta aaaaatgtca aaattgtaat | 5340 |
| gagcaagcat gtacaagtag tcgtaaatca aaggttttaa acaggactgc attttcaatt | 5400 |
| aggaaaagct gtttggcaga tagcatccaa tgcaaaaaca gaaatatcgt aacgttctgc | 5460 |
| ttagtgggca agataagata ggaaagacat gctcaaagag gcaaagaat cattgctatc | 5520 |
| attcattcta cactagtttg aagaagtttt tgtacatcag agcacttcct tcagcacact | 5580 |
| tttttgcctt cagatttcat tttttataaa atgagaagac taatgataaa ctgtagaaat | 5640 |
| caaaatttat tgagaaatct gtttctccta acagatagta accctgccat gatatactac | 5700 |
| ttcaacaatg ttataaaatt tatgtgataa tatacatttt aacctgggat ttctaaattg | 5760 |
| ctttaacaaa tgctaatcct gagagttgcc ctgcaggact caaaagggaa aggttttggg | 5820 |
| acgtggcaga accctgcagg gacatggaat taaggccatt gcaatgtatc atctttgtag | 5880 |
| cattgtcatc actcctaagc tgccttcaca gttttagtac actaagatga ggaaatcgaa | 5940 |
| aatgggcaga gaaagctcat actgtataat tgaagacagt gacagagaac gtgtcagtta | 6000 |
| tgccaaaact cttttgattt ctgttccagg atttccaaca agaggggaaa ggaatgactt | 6060 |
| gggagggtgg gaaagacatt aggagttgtt tttattttt accttggaag ctttagctac | 6120 |
| caatccagta ccctcctaac tagaatgtat acacatcagc aggactgact gactacttca | 6180 |
| ttagagatat actgtactca ttgggggcct tgggggtact gctgttctta tgtgggattt | 6240 |
| taatgttgta atgtattgca tcttaatgta ttgaattcat tttgttgtac tatattggtt | 6300 |
| ggcattttat taaataaat tgtattgtat catatttgta tgttttaaga gaaaataata | 6360 |
| taaaatacaa tatttgtact attatatagt gcaaaaacta caaatctgtg cctctgcctc | 6420 |
| ttgaattaat tctttggttg cttgcatttg ggaagggaat ggagaaagga aagaaccaat | 6480 |
| aaagctttca aagttcaag | 6499 |

<210> SEQ ID NO 2
<211> LENGTH: 687
<212> TYPE: PRT
<213> ORGANISM: Homo sapiens

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
```

```
            130                 135                 140
Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
                180                 185                 190

Ile Ile Ser Asn Ala Thr Tyr Lys Glu Ile Gly Leu Leu Thr Cys Glu
                195                 200                 205

Ala Thr Val Asn Gly His Leu Tyr Lys Thr Asn Tyr Leu Thr His Arg
210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
                260                 265                 270

Asn Lys Arg Ala Ser Val Arg Arg Ile Asp Gln Ser Asn Ser His
275                 280                 285

Ala Asn Ile Phe Tyr Ser Val Leu Thr Ile Asp Lys Met Gln Asn Lys
290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
                340                 345                 350

Tyr Arg Leu Ser Met Lys Val Lys Ala Phe Pro Ser Pro Glu Val Val
                355                 360                 365

Trp Leu Lys Asp Gly Leu Pro Ala Thr Glu Lys Ser Ala Arg Tyr Leu
                370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
                420                 425                 430

Lys Ala Val Ser Ser Phe Pro Asp Pro Ala Leu Tyr Pro Leu Gly Ser
                435                 440                 445

Arg Gln Ile Leu Thr Cys Thr Ala Tyr Gly Ile Pro Gln Pro Thr Ile
                450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
                500                 505                 510

Glu Gly Lys Asn Lys Met Ala Ser Thr Leu Val Val Ala Asp Ser Arg
                515                 520                 525

Ile Ser Gly Ile Tyr Ile Cys Ile Ala Ser Asn Lys Val Gly Thr Val
                530                 535                 540

Gly Arg Asn Ile Ser Phe Tyr Ile Thr Asp Val Pro Asn Gly Phe His
545                 550                 555                 560
```

```
Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
        675                 680                 685
```

<210> SEQ ID NO 3
<211> LENGTH: 733
<212> TYPE: PRT
<213> ORGANISM: Mus musculus

<400> SEQUENCE: 3

```
Ser Lys Leu Lys Val Pro Glu Leu Ser Leu Lys Gly Thr Gln His Val
1               5                   10                  15

Met Gln Ala Gly Gln Thr Leu Phe Leu Lys Cys Arg Gly Glu Ala Ala
                20                  25                  30

His Ser Trp Ser Leu Pro Thr Thr Val Ser Gln Glu Asp Lys Arg Leu
            35                  40                  45

Ser Ile Thr Pro Pro Ser Ala Cys Gly Arg Asp Asn Arg Gln Phe Cys
        50                  55                  60

Ser Thr Leu Thr Leu Asp Thr Ala Gln Ala Asn His Thr Gly Leu Tyr
65                  70                  75                  80

Thr Cys Arg Tyr Leu Pro Thr Ser Thr Ser Lys Lys Lys Lys Ala Glu
                85                  90                  95

Ser Ser Ile Tyr Ile Phe Val Ser Asp Ala Gly Ser Pro Phe Ile Glu
                100                 105                 110

Met His Thr Asp Ile Pro Lys Leu Val His Met Thr Glu Gly Arg Gln
            115                 120                 125

Leu Ile Ile Pro Cys Arg Val Thr Ser Pro Asn Val Thr Val Thr Leu
        130                 135                 140

Lys Lys Phe Pro Phe Asp Thr Leu Thr Pro Asp Gly Gln Arg Ile Thr
145                 150                 155                 160

Trp Asp Ser Arg Arg Gly Phe Ile Ile Ala Asn Ala Thr Tyr Lys Glu
                165                 170                 175

Ile Gly Leu Leu Asn Cys Glu Ala Thr Val Asn Gly His Leu Tyr Gln
            180                 185                 190

Thr Asn Tyr Leu Thr His Arg Gln Thr Asn Thr Ile Leu Asp Val Gln
        195                 200                 205

Ile Arg Pro Pro Ser Pro Val Arg Leu Leu His Gly Gln Thr Leu Val
        210                 215                 220

Leu Asn Cys Thr Ala Thr Thr Glu Leu Asn Thr Arg Val Gln Met Ser
225                 230                 235                 240

Trp Asn Tyr Pro Gly Lys Ala Thr Lys Arg Ala Ser Ile Arg Gln Arg
```

```
                    245                 250                 255
Ile Asp Arg Ser His Ser His Asn Asn Val Phe His Ser Val Leu Lys
            260                 265                 270
Ile Asn Val Glu Ser Arg Asp Lys Gly Leu Tyr Thr Cys Arg Val
        275                 280                 285
Lys Ser Gly Ser Ser Phe Gln Ser Phe Asn Thr Ser Val His Val Tyr
    290                 295                 300
Glu Lys Gly Phe Ile Ser Val Lys His Arg Lys Gln Pro Val Gln Glu
305                 310                 315                 320
Thr Thr Ala Gly Arg Arg Ser Tyr Arg Leu Ser Met Lys Val Lys Ala
                325                 330                 335
Phe Pro Ser Pro Glu Ile Val Trp Leu Lys Asp Gly Ser Pro Ala Thr
            340                 345                 350
Leu Lys Ser Ala Arg Tyr Leu Val His Gly Tyr Ser Leu Ile Ile Lys
        355                 360                 365
Asp Val Thr Thr Glu Asp Ala Gly Asp Tyr Thr Ile Leu Leu Gly Ile
    370                 375                 380
Lys Gln Ser Arg Leu Phe Lys Asn Leu Thr Ala Thr Leu Ile Val Asn
385                 390                 395                 400
Val Lys Pro Gln Ile Tyr Glu Lys Ser Val Ser Ser Leu Pro Ser Pro
                405                 410                 415
Pro Leu Tyr Pro Leu Gly Ser Arg Gln Val Leu Thr Cys Thr Val Tyr
            420                 425                 430
Gly Ile Pro Arg Pro Thr Ile Thr Trp Leu Trp His Pro Cys His His
        435                 440                 445
Asn His Ser Lys Glu Arg Tyr Asp Phe Cys Thr Glu Asn Glu Glu Ser
    450                 455                 460
Phe Ile Leu Asp Pro Ser Ser Asn Leu Gly Asn Arg Ile Glu Ser Ile
465                 470                 475                 480
Ser Gln Arg Met Thr Val Ile Glu Gly Thr Asn Lys Thr Val Ser Thr
                485                 490                 495
Leu Val Val Ala Asp Ser Gln Thr Pro Gly Ile Tyr Ser Cys Arg Ala
            500                 505                 510
Phe Asn Lys Ile Gly Thr Val Glu Arg Asn Ile Lys Phe Tyr Val Thr
        515                 520                 525
Asp Val Pro Asn Gly Phe His Val Ser Leu Glu Lys Met Pro Ala Glu
    530                 535                 540
Gly Glu Asp Leu Lys Leu Ser Cys Val Asn Lys Phe Leu Tyr Arg
545                 550                 555                 560
Asp Ile Thr Trp Ile Leu Leu Arg Thr Val Asn Asn Arg Thr Met His
                565                 570                 575
His Ser Ile Ser Lys Gln Lys Met Ala Thr Thr Gln Asp Tyr Ser Ile
            580                 585                 590
Thr Leu Asn Leu Val Ile Lys Asn Val Ser Leu Glu Asp Ser Gly Thr
        595                 600                 605
Tyr Ala Cys Arg Ala Arg Asn Ile Tyr Thr Gly Glu Asp Ile Leu Arg
    610                 615                 620
Lys Thr Glu Val Leu Val Arg Asp Ser Glu Ala Pro His Leu Leu Gln
625                 630                 635                 640
Asn Leu Ser Asp Tyr Glu Val Ser Ile Ser Gly Ser Thr Thr Leu Asp
                645                 650                 655
Cys Gln Ala Arg Gly Val Pro Ala Pro Gln Ile Thr Trp Phe Lys Asn
            660                 665                 670
```

```
Asn His Lys Ile Gln Gln Glu Pro Gly Ile Ile Leu Gly Pro Gly Asn
            675                 680                 685

Ser Thr Leu Phe Ile Glu Arg Val Thr Glu Glu Asp Glu Gly Val Tyr
        690                 695                 700

Arg Cys Arg Ala Thr Asn Gln Lys Gly Ala Val Glu Ser Ala Ala Tyr
705                 710                 715                 720

Leu Thr Val Gln Gly Thr Ser Asp Lys Ser Asn Leu Glu
                725                 730

<210> SEQ ID NO 4
<211> LENGTH: 630
<212> TYPE: PRT
<213> ORGANISM: Homo sapiens

<400> SEQUENCE: 4

Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Lys Glu Thr Glu Ser
                85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125

Val Ile Pro Cys Arg Val Thr Ser Pro Asn Ile Thr Val Thr Leu Lys
    130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Gln Ile
        195                 200                 205

Ser Thr Pro Arg Pro Val Lys Leu Leu Arg Gly His Thr Leu Val Leu
    210                 215                 220

Asn Cys Thr Ala Thr Thr Pro Leu Asn Thr Arg Val Gln Met Thr Trp
225                 230                 235                 240

Ser Tyr Pro Asp Glu Lys Asn Lys Arg Ala Ser Val Arg Arg Arg Ile
                245                 250                 255

Asp Gln Ser Asn Ser His Ala Asn Ile Phe Tyr Ser Val Leu Thr Ile
            260                 265                 270

Asp Lys Met Gln Asn Lys Asp Lys Gly Leu Tyr Thr Cys Arg Val Arg
        275                 280                 285

Ser Gly Pro Ser Phe Lys Ser Val Asn Thr Ser Val His Ile Tyr Asp
    290                 295                 300

Lys Ala Phe Ile Thr Val Lys His Arg Lys Gln Gln Val Leu Glu Thr
```

-continued

```
                305                 310                 315                 320
    Val Ala Gly Lys Arg Ser Tyr Arg Leu Ser Met Lys Val Lys Ala Phe
                    325                 330                 335

Pro Ser Pro Glu Val Val Trp Leu Lys Asp Gly Leu Pro Ala Thr Glu
                    340                 345                 350

Lys Ser Ala Arg Tyr Leu Thr Arg Gly Tyr Ser Leu Ile Ile Lys Asp
                    355                 360                 365

Val Thr Glu Glu Asp Ala Gly Asn Tyr Thr Ile Leu Leu Ser Ile Lys
                    370                 375                 380

Gln Ser Asn Val Phe Lys Asn Leu Thr Ala Thr Leu Ile Val Asn Val
    385                 390                 395                 400

Lys Pro Gln Ile Tyr Glu Lys Ala Val Ser Ser Phe Pro Asp Pro Ala
                    405                 410                 415

Leu Tyr Pro Leu Gly Ser Arg Gln Ile Leu Thr Cys Thr Ala Tyr Gly
                    420                 425                 430

Ile Pro Gln Pro Thr Ile Lys Trp Phe Trp His Pro Cys Asn His Asn
                    435                 440                 445

His Ser Glu Ala Arg Cys Asp Phe Cys Ser Asn Asn Glu Glu Ser Phe
                    450                 455                 460

Ile Leu Asp Ala Asp Ser Asn Met Gly Asn Arg Ile Glu Ser Ile Thr
    465                 470                 475                 480

Gln Arg Met Ala Ile Ile Glu Gly Lys Asn Lys Met Ala Ser Thr Leu
                    485                 490                 495

Val Val Ala Asp Ser Arg Ile Ser Gly Ile Tyr Ile Cys Ile Ala Ser
                    500                 505                 510

Asn Lys Val Gly Thr Val Gly Arg Asn Ile Ser Phe Tyr Ile Thr Asp
                    515                 520                 525

Val Pro Asn Gly Phe His Val Asn Leu Glu Lys Met Pro Thr Glu Gly
                    530                 535                 540

Glu Asp Leu Lys Leu Ser Cys Thr Val Asn Lys Phe Leu Tyr Arg Asp
    545                 550                 555                 560

Val Thr Trp Ile Leu Leu Arg Thr Val Asn Asn Arg Thr Met His Tyr
                    565                 570                 575

Ser Ile Ser Lys Gln Lys Met Ala Ile Thr Lys Glu His Ser Ile Thr
                    580                 585                 590

Leu Asn Leu Thr Ile Met Asn Val Ser Leu Gln Asp Ser Gly Thr Tyr
                    595                 600                 605

Ala Cys Arg Ala Arg Asn Val Tyr Thr Gly Glu Glu Ile Leu Gln Lys
                    610                 615                 620

Lys Glu Ile Thr Ile Arg
    625                 630

<210> SEQ ID NO 5
<211> LENGTH: 733
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
                20                  25                  30
```

-continued

```
Glu Leu Ser Leu Lys Gly Thr Gln His Ile Met Gln Ala Gly Gln Thr
         35                  40                  45
Leu His Leu Gln Cys Arg Gly Glu Ala Ala His Lys Trp Ser Leu Pro
 50                  55                  60
Glu Met Val Ser Lys Glu Ser Glu Arg Leu Ser Ile Thr Lys Ser Ala
 65                  70                  75                  80
Cys Gly Arg Asn Gly Lys Gln Phe Cys Ser Thr Leu Thr Leu Asn Thr
                 85                  90                  95
Ala Gln Ala Asn His Thr Gly Phe Tyr Ser Cys Lys Tyr Leu Ala Val
                100                 105                 110
Pro Thr Ser Lys Lys Lys Glu Thr Glu Ser Ala Ile Tyr Ile Phe Ile
                115                 120                 125
Ser Asp Thr Gly Arg Pro Phe Val Glu Met Tyr Ser Glu Ile Pro Glu
130                 135                 140
Ile Ile His Met Thr Glu Gly Arg Glu Leu Val Ile Pro Cys Arg Val
145                 150                 155                 160
Thr Ser Pro Asn Ile Thr Val Thr Leu Lys Lys Phe Pro Leu Asp Thr
                165                 170                 175
Leu Ile Pro Asp Gly Lys Arg Ile Ile Trp Asp Ser Arg Lys Gly Phe
                180                 185                 190
Ile Ile Ser Asn Ala Thr Tyr Lys Glu Ile Gly Leu Leu Thr Cys Glu
                195                 200                 205
Ala Thr Val Asn Gly His Leu Tyr Lys Thr Asn Tyr Leu Thr His Arg
                210                 215                 220
Gln Thr Asn Thr Ile Ile Asp Val Gln Ile Ser Thr Pro Arg Pro Val
225                 230                 235                 240
Lys Leu Leu Arg Gly His Thr Leu Val Leu Asn Cys Thr Ala Thr Thr
                245                 250                 255
Pro Leu Asn Thr Arg Val Gln Met Thr Trp Ser Tyr Pro Asp Glu Lys
                260                 265                 270
Asn Lys Arg Ala Ser Val Arg Arg Ile Asp Gln Ser Asn Ser His
                275                 280                 285
Ala Asn Ile Phe Tyr Ser Val Leu Thr Ile Asp Lys Met Gln Asn Lys
                290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
                325                 330                 335
Lys His Arg Lys Gln Gln Val Leu Glu Thr Val Ala Gly Lys Arg Ser
                340                 345                 350
Tyr Arg Leu Ser Met Lys Val Lys Ala Phe Pro Ser Pro Glu Val Val
                355                 360                 365
Trp Leu Lys Asp Gly Leu Pro Ala Thr Glu Lys Ser Ala Arg Tyr Leu
370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
                405                 410                 415
Asn Leu Thr Ala Thr Leu Ile Val Asn Val Lys Pro Gln Ile Tyr Glu
                420                 425                 430
Lys Ala Val Ser Ser Phe Pro Asp Pro Ala Leu Tyr Pro Leu Gly Ser
                435                 440                 445
```

-continued

```
Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val
            660                 665                 670

Ala Ile Ser Ser Ser Thr Thr Leu Asp Cys His Ala Asn Gly Val Pro
        675                 680                 685

Glu Pro Gln Ile Thr Trp Phe Lys Asn Asn His Lys Ile Gln Gln Glu
    690                 695                 700

Pro Glu Leu Tyr Thr Ser Thr Ser Pro Ser Ser Ser Ser Ser Ser Pro
705                 710                 715                 720

Leu Ser Ser Ser Ser Ser Ser Ser Ser Ser Ser
                725                 730
```

<210> SEQ ID NO 6
<211> LENGTH: 639
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 6

```
Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
```

```
            65                  70                  75                  80
        Cys Lys Tyr Leu Ala Val Pro Thr Ser Lys Lys Glu Thr Glu Ser
                         85                  90                  95
        Ala Ile Tyr Ile Phe Ile Ser Asp Thr Gly Arg Pro Phe Val Glu Met
                        100                 105                 110
        Tyr Ser Glu Ile Pro Glu Ile His Met Thr Glu Gly Arg Glu Leu
                    115                 120                 125
        Val Ile Pro Cys Arg Val Thr Ser Pro Asn Ile Thr Val Thr Leu Lys
                    130                 135                 140
        Lys Phe Pro Leu Asp Thr Leu Ile Pro Asp Gly Lys Arg Ile Ile Trp
        145                 150                 155                 160
        Asp Ser Arg Lys Gly Phe Ile Ile Ser Asn Ala Thr Tyr Lys Glu Ile
                        165                 170                 175
        Gly Leu Leu Thr Cys Glu Ala Thr Val Asn Gly His Leu Tyr Lys Thr
                        180                 185                 190
        Asn Tyr Leu Thr His Arg Gln Thr Asn Thr Ile Ile Asp Val Gln Ile
                    195                 200                 205
        Ser Thr Pro Arg Pro Val Lys Leu Leu Arg Gly His Thr Leu Val Leu
                    210                 215                 220
        Asn Cys Thr Ala Thr Thr Pro Leu Asn Thr Arg Val Gln Met Thr Trp
        225                 230                 235                 240
        Ser Tyr Pro Asp Glu Lys Asn Lys Arg Ala Ser Val Arg Arg Ile
                        245                 250                 255
        Asp Gln Ser Asn Ser His Ala Asn Ile Phe Tyr Ser Val Leu Thr Ile
                        260                 265                 270
        Asp Lys Met Gln Asn Lys Asp Lys Gly Leu Tyr Thr Cys Arg Val Arg
                    275                 280                 285
        Ser Gly Pro Ser Phe Lys Ser Val Asn Thr Ser Val His Ile Tyr Asp
                    290                 295                 300
        Lys Ala Phe Ile Thr Val Lys His Arg Lys Gln Gln Val Leu Glu Thr
        305                 310                 315                 320
        Val Ala Gly Lys Arg Ser Tyr Arg Leu Ser Met Lys Val Lys Ala Phe
                        325                 330                 335
        Pro Ser Pro Glu Val Val Trp Leu Lys Asp Gly Leu Pro Ala Thr Glu
                        340                 345                 350
        Lys Ser Ala Arg Tyr Leu Thr Arg Gly Tyr Ser Leu Ile Ile Lys Asp
                    355                 360                 365
        Val Thr Glu Glu Asp Ala Gly Asn Tyr Thr Ile Leu Leu Ser Ile Lys
                    370                 375                 380
        Gln Ser Asn Val Phe Lys Asn Leu Thr Ala Thr Leu Ile Val Asn Val
        385                 390                 395                 400
        Lys Pro Gln Ile Tyr Glu Lys Ala Val Ser Ser Phe Pro Asp Pro Ala
                        405                 410                 415
        Leu Tyr Pro Leu Gly Ser Arg Gln Ile Leu Thr Cys Thr Ala Tyr Gly
                        420                 425                 430
        Ile Pro Gln Pro Thr Ile Lys Trp Phe Trp His Pro Cys Asn His Asn
                    435                 440                 445
        His Ser Glu Ala Arg Cys Asp Phe Cys Ser Asn Asn Glu Glu Ser Phe
                    450                 455                 460
        Ile Leu Asp Ala Asp Ser Asn Met Gly Asn Arg Ile Glu Ser Ile Thr
        465                 470                 475                 480
        Gln Arg Met Ala Ile Ile Glu Gly Lys Asn Lys Met Ala Ser Thr Leu
                        485                 490                 495
```

Val Val Ala Asp Ser Arg Ile Ser Gly Ile Tyr Ile Cys Ile Ala Ser
            500                 505                 510

Asn Lys Val Gly Thr Val Gly Arg Asn Ile Ser Phe Tyr Ile Thr Asp
            515                 520                 525

Val Pro Asn Gly Phe His Val Asn Leu Glu Lys Met Pro Thr Glu Gly
            530                 535                 540

Glu Asp Leu Lys Leu Ser Cys Thr Val Asn Lys Phe Leu Tyr Arg Asp
545                 550                 555                 560

Val Thr Trp Ile Leu Leu Arg Thr Val Asn Asn Arg Thr Met His Tyr
                565                 570                 575

Ser Ile Ser Lys Gln Lys Met Ala Ile Thr Lys Glu His Ser Ile Thr
            580                 585                 590

Leu Asn Leu Thr Ile Met Asn Val Ser Leu Gln Asp Ser Gly Thr Tyr
            595                 600                 605

Ala Cys Arg Ala Arg Asn Val Tyr Thr Gly Glu Glu Ile Leu Gln Lys
            610                 615                 620

Lys Glu Ile Thr Ile Arg Asp Gln Glu Ala Ile Gln Gln Glu Pro
625                 630                 635

<210> SEQ ID NO 7
<211> LENGTH: 667
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 7

Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Lys Glu Thr Glu Ser
                85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125

Val Ile Pro Cys Arg Val Thr Ser Pro Asn Ile Thr Val Thr Leu Lys
    130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Gln Ile
        195                 200                 205

```
Ser Thr Pro Arg Pro Val Lys Leu Leu Arg Gly His Thr Leu Val Leu
210                 215                 220

Asn Cys Thr Ala Thr Thr Pro Leu Asn Thr Arg Val Gln Met Thr Trp
225                 230                 235                 240

Ser Tyr Pro Asp Glu Lys Asn Lys Arg Ala Ser Val Arg Arg Ile
                245                 250                 255

Asp Gln Ser Asn Ser His Ala Asn Ile Phe Tyr Ser Val Leu Thr Ile
                260                 265                 270

Asp Lys Met Gln Asn Lys Asp Lys Gly Leu Tyr Thr Cys Arg Val Arg
                275                 280                 285

Ser Gly Pro Ser Phe Lys Ser Val Asn Thr Ser Val His Ile Tyr Asp
290                 295                 300

Lys Ala Phe Ile Thr Val Lys His Arg Lys Gln Gln Val Leu Glu Thr
305                 310                 315                 320

Val Ala Gly Lys Arg Ser Tyr Arg Leu Ser Met Lys Val Lys Ala Phe
                325                 330                 335

Pro Ser Pro Glu Val Val Trp Leu Lys Asp Gly Leu Pro Ala Thr Glu
                340                 345                 350

Lys Ser Ala Arg Tyr Leu Thr Arg Gly Tyr Ser Leu Ile Ile Lys Asp
                355                 360                 365

Val Thr Glu Glu Asp Ala Gly Asn Tyr Thr Ile Leu Leu Ser Ile Lys
370                 375                 380

Gln Ser Asn Val Phe Lys Asn Leu Thr Ala Thr Leu Ile Val Asn Val
385                 390                 395                 400

Lys Pro Gln Ile Tyr Glu Lys Ala Val Ser Ser Phe Pro Asp Pro Ala
                405                 410                 415

Leu Tyr Pro Leu Gly Ser Arg Gln Ile Leu Thr Cys Thr Ala Tyr Gly
                420                 425                 430

Ile Pro Gln Pro Thr Ile Lys Trp Phe Trp His Pro Cys Asn His Asn
                435                 440                 445

His Ser Glu Ala Arg Cys Asp Phe Cys Ser Asn Asn Glu Glu Ser Phe
450                 455                 460

Ile Leu Asp Ala Asp Ser Asn Met Gly Asn Arg Ile Glu Ser Ile Thr
465                 470                 475                 480

Gln Arg Met Ala Ile Ile Glu Gly Lys Asn Lys Met Ala Ser Thr Leu
                485                 490                 495

Val Val Ala Asp Ser Arg Ile Ser Gly Ile Tyr Ile Cys Ile Ala Ser
                500                 505                 510

Asn Lys Val Gly Thr Val Gly Arg Asn Ile Ser Phe Tyr Ile Thr Asp
                515                 520                 525

Val Pro Asn Gly Phe His Val Asn Leu Glu Lys Met Pro Thr Glu Gly
530                 535                 540

Glu Asp Leu Lys Leu Ser Cys Thr Val Asn Lys Phe Leu Tyr Arg Asp
545                 550                 555                 560

Val Thr Trp Ile Leu Leu Arg Thr Val Asn Asn Arg Thr Met His Tyr
                565                 570                 575

Ser Ile Ser Lys Gln Lys Met Ala Ile Thr Lys Glu His Ser Ile Thr
                580                 585                 590

Leu Asn Leu Thr Ile Met Asn Val Ser Leu Gln Asp Ser Gly Thr Tyr
                595                 600                 605

Ala Cys Arg Ala Arg Asn Val Tyr Thr Gly Glu Glu Ile Leu Gln Lys
                610                 615                 620

Lys Glu Ile Thr Ile Arg Asp Gln Glu Ala Ile Gln Gln Glu Pro Glu
```

```
                625                 630                 635                 640
Leu Tyr Thr Ser Thr Ser Pro Ser Ser Ser Ser Ser Pro Leu Ser
                    645                 650                 655
Ser Ser Ser Ser Ser Ser Ser Ser Ser Ser
                660                 665

<210> SEQ ID NO 8
<211> LENGTH: 541
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320
```

```
Ser Val Asn Thr Ser Val His Ile Tyr Asp Lys Ala Phe Ile Thr Val
            325                 330                 335

Lys His Arg Lys Gln Gln Val Leu Glu Thr Val Ala Gly Lys Arg Ser
        340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
        370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
            405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
            435                 440                 445

Arg Gln Ile Leu Thr Cys Thr Ala Tyr Gly Ile Pro Gln Pro Thr Ile
        450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
            485                 490                 495

Asn Met Gly Asn Arg Ile Glu Ser Ile Thr Gln Arg Met Ala Ile Ile
            500                 505                 510

Glu Gly Lys Asn Lys Leu Pro Pro Ala Asn Ser Ser Phe Met Leu Pro
            515                 520                 525

Pro Thr Ser Phe Ser Ser Asn Tyr Phe His Phe Leu Pro
        530                 535                 540

<210> SEQ ID NO 9
<211> LENGTH: 491
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Lys Glu Thr Glu Ser
            85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125
```

```
Val Ile Pro Cys Arg Val Thr Ser Pro Asn Ile Thr Val Thr Leu Lys
130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
                180                 185                 190

Asn Tyr Leu Thr His Arg Gln Thr Asn Thr Ile Ile Asp Val Gln Ile
            195                 200                 205

Ser Thr Pro Arg Pro Val Lys Leu Leu Arg Gly His Thr Leu Val Leu
210                 215                 220

Asn Cys Thr Ala Thr Thr Pro Leu Asn Thr Arg Val Gln Met Thr Trp
225                 230                 235                 240

Ser Tyr Pro Asp Glu Lys Asn Lys Arg Ala Ser Val Arg Arg Arg Ile
                245                 250                 255

Asp Gln Ser Asn Ser His Ala Asn Ile Phe Tyr Ser Val Leu Thr Ile
                260                 265                 270

Asp Lys Met Gln Asn Lys Asp Lys Gly Leu Tyr Thr Cys Arg Val Arg
            275                 280                 285

Ser Gly Pro Ser Phe Lys Ser Val Asn Thr Ser Val His Ile Tyr Asp
290                 295                 300

Lys Ala Phe Ile Thr Val Lys His Arg Lys Gln Gln Val Leu Glu Thr
305                 310                 315                 320

Val Ala Gly Lys Arg Ser Tyr Arg Leu Ser Met Lys Val Lys Ala Phe
                325                 330                 335

Pro Ser Pro Glu Val Val Trp Leu Lys Asp Gly Leu Pro Ala Thr Glu
                340                 345                 350

Lys Ser Ala Arg Tyr Leu Thr Arg Gly Tyr Ser Leu Ile Ile Lys Asp
            355                 360                 365

Val Thr Glu Glu Asp Ala Gly Asn Tyr Thr Ile Leu Leu Ser Ile Lys
370                 375                 380

Gln Ser Asn Val Phe Lys Asn Leu Thr Ala Thr Leu Ile Val Asn Val
385                 390                 395                 400

Lys Pro Gln Ile Tyr Glu Lys Ala Val Ser Ser Phe Pro Asp Pro Ala
                405                 410                 415

Leu Tyr Pro Leu Gly Ser Arg Gln Ile Leu Thr Cys Thr Ala Tyr Gly
                420                 425                 430

Ile Pro Gln Pro Thr Ile Lys Trp Phe Trp His Pro Cys Asn His Asn
            435                 440                 445

His Ser Glu Ala Arg Cys Asp Phe Cys Ser Asn Asn Glu Glu Ser Phe
450                 455                 460

Ile Leu Asp Ala Asp Ser Asn Met Gly Asn Arg Ile Glu Ser Ile Thr
465                 470                 475                 480

Gln Arg Met Ala Ile Ile Glu Gly Lys Asn Lys
                485                 490
```

<210> SEQ ID NO 10
<211> LENGTH: 515
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 10

```
Ser Lys Leu Lys Asp Pro Glu Leu Ser Leu Lys Gly Thr Gln His Ile
1               5                   10                  15

Met Gln Ala Gly Gln Thr Leu His Leu Gln Cys Arg Gly Glu Ala Ala
            20                  25                  30

His Lys Trp Ser Leu Pro Glu Met Val Ser Lys Glu Ser Glu Arg Leu
        35                  40                  45

Ser Ile Thr Lys Ser Ala Cys Gly Arg Asn Gly Lys Gln Phe Cys Ser
    50                  55                  60

Thr Leu Thr Leu Asn Thr Ala Gln Ala Asn His Thr Gly Phe Tyr Ser
65                  70                  75                  80

Cys Lys Tyr Leu Ala Val Pro Thr Ser Lys Lys Lys Glu Thr Glu Ser
                85                  90                  95

Ala Ile Tyr Ile Phe Ile Ser Asp Thr Gly Arg Pro Phe Val Glu Met
            100                 105                 110

Tyr Ser Glu Ile Pro Glu Ile Ile His Met Thr Glu Gly Arg Glu Leu
        115                 120                 125

Val Ile Pro Cys Arg Val Thr Ser Pro Asn Ile Thr Val Thr Leu Lys
130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Gln Ile
        195                 200                 205

Ser Thr Pro Arg Pro Val Lys Leu Leu Arg Gly His Thr Leu Val Leu
    210                 215                 220

Asn Cys Thr Ala Thr Thr Pro Leu Asn Thr Arg Val Gln Met Thr Trp
225                 230                 235                 240

Ser Tyr Pro Asp Glu Lys Asn Lys Arg Ala Ser Val Arg Arg Arg Ile
                245                 250                 255

Asp Gln Ser Asn Ser His Ala Asn Ile Phe Tyr Ser Val Leu Thr Ile
            260                 265                 270

Asp Lys Met Gln Asn Lys Asp Lys Gly Leu Tyr Thr Cys Arg Val Arg
        275                 280                 285

Ser Gly Pro Ser Phe Lys Ser Val Asn Thr Ser Val His Ile Tyr Asp
    290                 295                 300

Lys Ala Phe Ile Thr Val Lys His Arg Lys Gln Gln Val Leu Glu Thr
305                 310                 315                 320

Val Ala Gly Lys Arg Ser Tyr Arg Leu Ser Met Lys Val Lys Ala Phe
                325                 330                 335

Pro Ser Pro Glu Val Val Trp Leu Lys Asp Gly Leu Pro Ala Thr Glu
            340                 345                 350

Lys Ser Ala Arg Tyr Leu Thr Arg Gly Tyr Ser Leu Ile Ile Lys Asp
        355                 360                 365

Val Thr Glu Glu Asp Ala Gly Asn Tyr Thr Ile Leu Leu Ser Ile Lys
    370                 375                 380

Gln Ser Asn Val Phe Lys Asn Leu Thr Ala Thr Leu Ile Val Asn Val
385                 390                 395                 400

Lys Pro Gln Ile Tyr Glu Lys Ala Val Ser Ser Phe Pro Asp Pro Ala
                405                 410                 415
```

```
Leu Tyr Pro Leu Gly Ser Arg Gln Ile Leu Thr Cys Thr Ala Tyr Gly
                420                 425                 430

Ile Pro Gln Pro Thr Ile Lys Trp Phe Trp His Pro Cys Asn His Asn
            435                 440                 445

His Ser Glu Ala Arg Cys Asp Phe Cys Ser Asn Asn Glu Glu Ser Phe
        450                 455                 460

Ile Leu Asp Ala Asp Ser Asn Met Gly Asn Arg Ile Glu Ser Ile Thr
465                 470                 475                 480

Gln Arg Met Ala Ile Ile Glu Gly Lys Asn Lys Leu Pro Pro Ala Asn
                485                 490                 495

Ser Ser Phe Met Leu Pro Pro Thr Ser Phe Ser Ser Asn Tyr Phe His
            500                 505                 510

Phe Leu Pro
        515

<210> SEQ ID NO 11
<211> LENGTH: 1338
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 11

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240
```

-continued

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
        275                 280                 285

Ala Asn Ile Phe Tyr Ser Val Leu Thr Ile Asp Lys Met Gln Asn Lys
        290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
            500                 505                 510

Glu Gly Lys Asn Lys Met Ala Ser Thr Leu Val Val Ala Asp Ser Arg
        515                 520                 525

Ile Ser Gly Ile Tyr Ile Cys Ile Ala Ser Asn Lys Val Gly Thr Val
    530                 535                 540

Gly Arg Asn Ile Ser Phe Tyr Ile Thr Asp Val Pro Asn Gly Phe His
545                 550                 555                 560

Val Asn Leu Glu Lys Met Pro Thr Glu Gly Glu Asp Leu Lys Leu Ser
                565                 570                 575

Cys Thr Val Asn Lys Phe Leu Tyr Arg Asp Val Thr Trp Ile Leu Leu
            580                 585                 590

Arg Thr Val Asn Asn Arg Thr Met His Tyr Ser Ile Ser Lys Gln Lys
        595                 600                 605

Met Ala Ile Thr Lys Glu His Ser Ile Thr Leu Asn Leu Thr Ile Met
    610                 615                 620

Asn Val Ser Leu Gln Asp Ser Gly Thr Tyr Ala Cys Arg Ala Arg Asn
625                 630                 635                 640

Val Tyr Thr Gly Glu Glu Ile Leu Gln Lys Lys Glu Ile Thr Ile Arg
                645                 650                 655

Asp Gln Glu Ala Pro Tyr Leu Leu Arg Asn Leu Ser Asp His Thr Val

-continued

```
                    660                 665                 670
Ala Ile Ser Ser Ser Thr Thr Leu Asp Cys His Ala Asn Gly Val Pro
            675                 680                 685

Glu Pro Gln Ile Thr Trp Phe Lys Asn Asn His Lys Ile Gln Gln Glu
690                 695                 700

Pro Gly Ile Ile Leu Gly Pro Gly Ser Ser Thr Leu Phe Ile Glu Arg
705                 710                 715                 720

Val Thr Glu Glu Asp Glu Gly Val Tyr His Cys Lys Ala Thr Asn Gln
                    725                 730                 735

Lys Gly Ser Val Glu Ser Ser Ala Tyr Leu Thr Val Gln Gly Thr Ser
            740                 745                 750

Asp Lys Ser Asn Leu Glu Leu Ile Thr Leu Thr Cys Thr Cys Val Ala
            755                 760                 765

Ala Thr Leu Phe Trp Leu Leu Leu Thr Leu Phe Ile Arg Lys Met Lys
            770                 775                 780

Arg Ser Ser Ser Glu Ile Lys Thr Asp Tyr Leu Ser Ile Ile Met Asp
785                 790                 795                 800

Pro Asp Glu Val Pro Leu Asp Glu Gln Cys Glu Arg Leu Pro Tyr Asp
                    805                 810                 815

Ala Ser Lys Trp Glu Phe Ala Arg Glu Arg Leu Lys Leu Gly Lys Ser
            820                 825                 830

Leu Gly Arg Gly Ala Phe Gly Lys Val Val Gln Ala Ser Ala Phe Gly
            835                 840                 845

Ile Lys Lys Ser Pro Thr Cys Arg Thr Val Ala Val Lys Met Leu Lys
            850                 855                 860

Glu Gly Ala Thr Ala Ser Glu Tyr Lys Ala Leu Met Thr Glu Leu Lys
865                 870                 875                 880

Ile Leu Thr His Ile Gly His His Leu Asn Val Val Asn Leu Leu Gly
                    885                 890                 895

Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
            915                 920                 925

Phe Leu Asn Lys Asp Ala Ala Leu His Met Glu Pro Lys Lys Glu Lys
            930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                    965                 970                 975

Leu Ser Asp Val Glu Glu Glu Glu Asp Ser Asp Gly Phe Tyr Lys Glu
            980                 985                 990

Pro Ile Thr Met Glu Asp Leu Ile Ser Tyr Ser Phe Gln Val Ala Arg
            995                 1000                1005

Gly Met Glu Phe Leu Ser Ser Arg Lys Cys Ile His Arg Asp Leu
            1010                1015                1020

Ala Ala Arg Asn Ile Leu Leu Ser Glu Asn Asn Val Val Lys Ile
            1025                1030                1035

Cys Asp Phe Gly Leu Ala Arg Asp Ile Tyr Lys Asn Pro Asp Tyr
            1040                1045                1050

Val Arg Lys Gly Asp Thr Arg Leu Pro Leu Lys Trp Met Ala Pro
            1055                1060                1065

Glu Ser Ile Phe Asp Lys Ile Tyr Ser Thr Lys Ser Asp Val Trp
            1070                1075                1080
```

Ser Tyr Gly Val Leu Leu Trp Glu Ile Phe Ser Leu Gly Gly Ser
1085                1090                1095

Pro Tyr Pro Gly Val Gln Met Asp Glu Asp Phe Cys Ser Arg Leu
1100                1105                1110

Arg Glu Gly Met Arg Met Arg Ala Pro Glu Tyr Ser Thr Pro Glu
1115                1120                1125

Ile Tyr Gln Ile Met Leu Asp Cys Trp His Arg Asp Pro Lys Glu
1130                1135                1140

Arg Pro Arg Phe Ala Glu Leu Val Glu Lys Leu Gly Asp Leu Leu
1145                1150                1155

Gln Ala Asn Val Gln Asp Gly Lys Asp Tyr Ile Pro Ile Asn
1160                1165                1170

Ala Ile Leu Thr Gly Asn Ser Gly Phe Thr Tyr Ser Thr Pro Ala
1175                1180                1185

Phe Ser Glu Asp Phe Phe Lys Glu Ser Ile Ser Ala Pro Lys Phe
1190                1195                1200

Asn Ser Gly Ser Ser Asp Asp Val Arg Tyr Val Asn Ala Phe Lys
1205                1210                1215

Phe Met Ser Leu Glu Arg Ile Lys Thr Phe Glu Glu Leu Leu Pro
1220                1225                1230

Asn Ala Thr Ser Met Phe Asp Asp Tyr Gln Gly Asp Ser Ser Thr
1235                1240                1245

Leu Leu Ala Ser Pro Met Leu Lys Arg Phe Thr Trp Thr Asp Ser
1250                1255                1260

Lys Pro Lys Ala Ser Leu Lys Ile Asp Leu Arg Val Thr Ser Lys
1265                1270                1275

Ser Lys Glu Ser Gly Leu Ser Asp Val Ser Arg Pro Ser Phe Cys
1280                1285                1290

His Ser Ser Cys Gly His Val Ser Glu Gly Lys Arg Arg Phe Thr
1295                1300                1305

Tyr Asp His Ala Glu Leu Glu Arg Lys Ile Ala Cys Cys Ser Pro
1310                1315                1320

Pro Pro Asp Tyr Asn Ser Val Val Leu Tyr Ser Thr Pro Pro Ile
1325                1330                1335

<210> SEQ ID NO 12
<211> LENGTH: 758
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
                20                  25                  30

Glu Leu Ser Leu Lys Gly Thr Gln His Ile Met Gln Ala Gly Gln Thr
            35                  40                  45

Leu His Leu Gln Cys Arg Gly Glu Ala Ala His Lys Trp Ser Leu Pro
        50                  55                  60

Glu Met Val Ser Lys Glu Ser Glu Arg Leu Ser Ile Thr Lys Ser Ala
65                  70                  75                  80

```
Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
            115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
            195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Ile Asp Gln Ser Asn Ser His
            275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
            355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
            435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480

Asp Phe Cys Ser Asn Asn Glu Glu Ser Phe Ile Leu Asp Ala Asp Ser
                485                 490                 495

Asn Met Gly Asn Arg Ile Glu Ser Ile Thr Gln Arg Met Ala Ile Ile
```

```
                500             505             510
Glu Gly Lys Asn Lys Met Ala Ser Thr Leu Val Val Ala Asp Ser Arg
            515                 520             525
Ile Ser Gly Ile Tyr Ile Cys Ile Ala Ser Asn Lys Val Gly Thr Val
        530                 535             540
Gly Arg Asn Ile Ser Phe Tyr Ile Thr Asp Val Pro Asn Gly Phe His
545                 550             555             560
Val Asn Leu Glu Lys Met Pro Thr Gly Glu Asp Leu Lys Leu Ser
            565                 570             575
Cys Thr Val Asn Lys Phe Leu Tyr Arg Asp Val Thr Trp Ile Leu Leu
        580                 585             590
Arg Thr Val Asn Asn Arg Thr Met His Tyr Ser Ile Ser Lys Gln Lys
            595                 600             605
Met Ala Ile Thr Lys Glu His Ser Ile Thr Leu Asn Leu Thr Ile Met
        610                 615             620
Asn Val Ser Leu Gln Asp Ser Gly Thr Tyr Ala Cys Arg Ala Arg Asn
625                 630             635             640
Val Tyr Thr Gly Glu Glu Ile Leu Gln Lys Lys Glu Ile Thr Ile Arg
            645                 650             655
Asp Gln Glu Ala Pro Tyr Leu Leu Arg Asn Leu Ser Asp His Thr Val
        660                 665             670
Ala Ile Ser Ser Ser Thr Thr Leu Asp Cys His Ala Asn Gly Val Pro
            675                 680             685
Glu Pro Gln Ile Thr Trp Phe Lys Asn Asn His Lys Ile Gln Gln Glu
        690                 695             700
Pro Gly Ile Ile Leu Gly Pro Gly Ser Ser Thr Leu Phe Ile Glu Arg
705                 710             715             720
Val Thr Glu Glu Asp Glu Gly Val Tyr His Cys Lys Ala Thr Asn Gln
            725                 730             735
Lys Gly Ser Val Glu Ser Ser Ala Tyr Leu Thr Val Gln Gly Thr Ser
        740                 745             750
Asp Lys Ser Asn Leu Glu
        755

<210> SEQ ID NO 13
<211> LENGTH: 1312
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Ser Lys Leu Lys Asp Pro Glu Leu Ser Leu Lys Gly Thr Gln His Ile
1               5                   10              15
Met Gln Ala Gly Gln Thr Leu His Leu Gln Cys Arg Gly Glu Ala Ala
            20                  25              30
His Lys Trp Ser Leu Pro Glu Met Val Ser Lys Glu Ser Glu Arg Leu
        35                  40              45
Ser Ile Thr Lys Ser Ala Cys Gly Arg Asn Gly Lys Gln Phe Cys Ser
    50                  55              60
Thr Leu Thr Leu Asn Thr Ala Gln Ala Asn His Thr Gly Phe Tyr Ser
65              70                  75              80
Cys Lys Tyr Leu Ala Val Pro Thr Ser Lys Lys Lys Glu Thr Glu Ser
            85                  90              95
```

-continued

```
Ala Ile Tyr Ile Phe Ile Ser Asp Thr Gly Arg Pro Phe Val Glu Met
                100                 105                 110

Tyr Ser Glu Ile Pro Glu Ile His Met Thr Glu Gly Arg Glu Leu
            115                 120                 125

Val Ile Pro Cys Arg Val Thr Ser Pro Asn Ile Thr Val Thr Leu Lys
            130                 135                 140

Lys Phe Pro Leu Asp Thr Leu Ile Pro Asp Gly Lys Arg Ile Ile Trp
145                 150                 155                 160

Asp Ser Arg Lys Gly Phe Ile Ile Ser Asn Ala Thr Tyr Lys Glu Ile
                165                 170                 175

Gly Leu Leu Thr Cys Glu Ala Thr Val Asn Gly His Leu Tyr Lys Thr
            180                 185                 190

Asn Tyr Leu Thr His Arg Gln Thr Asn Thr Ile Ile Asp Val Gln Ile
            195                 200                 205

Ser Thr Pro Arg Pro Val Lys Leu Leu Arg Gly His Thr Leu Val Leu
    210                 215                 220

Asn Cys Thr Ala Thr Thr Pro Leu Asn Thr Arg Val Gln Met Thr Trp
225                 230                 235                 240

Ser Tyr Pro Asp Glu Lys Asn Lys Arg Ala Ser Val Arg Arg Arg Ile
                245                 250                 255

Asp Gln Ser Asn Ser His Ala Asn Ile Phe Tyr Ser Val Leu Thr Ile
            260                 265                 270

Asp Lys Met Gln Asn Lys Asp Lys Gly Leu Tyr Thr Cys Arg Val Arg
    275                 280                 285

Ser Gly Pro Ser Phe Lys Ser Val Asn Thr Ser Val His Ile Tyr Asp
    290                 295                 300

Lys Ala Phe Ile Thr Val Lys His Arg Lys Gln Gln Val Leu Glu Thr
305                 310                 315                 320

Val Ala Gly Lys Arg Ser Tyr Arg Leu Ser Met Lys Val Lys Ala Phe
                325                 330                 335

Pro Ser Pro Glu Val Val Trp Leu Lys Asp Gly Leu Pro Ala Thr Glu
            340                 345                 350

Lys Ser Ala Arg Tyr Leu Thr Arg Gly Tyr Ser Leu Ile Ile Lys Asp
            355                 360                 365

Val Thr Glu Glu Asp Ala Gly Asn Tyr Thr Ile Leu Leu Ser Ile Lys
    370                 375                 380

Gln Ser Asn Val Phe Lys Asn Leu Thr Ala Thr Leu Ile Val Asn Val
385                 390                 395                 400

Lys Pro Gln Ile Tyr Glu Lys Ala Val Ser Phe Pro Asp Pro Ala
                405                 410                 415

Leu Tyr Pro Leu Gly Ser Arg Gln Ile Leu Thr Cys Thr Ala Tyr Gly
            420                 425                 430

Ile Pro Gln Pro Thr Ile Lys Trp Phe Trp His Pro Cys Asn His Asn
            435                 440                 445

His Ser Glu Ala Arg Cys Asp Phe Cys Ser Asn Asn Glu Glu Ser Phe
    450                 455                 460

Ile Leu Asp Ala Asp Ser Asn Met Gly Asn Arg Ile Glu Ser Ile Thr
465                 470                 475                 480

Gln Arg Met Ala Ile Ile Glu Gly Lys Asn Lys Met Ala Ser Thr Leu
                485                 490                 495

Val Val Ala Asp Ser Arg Ile Ser Gly Ile Tyr Ile Cys Ile Ala Ser
            500                 505                 510
```

-continued

Asn Lys Val Gly Thr Val Gly Arg Asn Ile Ser Phe Tyr Ile Thr Asp
            515                 520                 525

Val Pro Asn Gly Phe His Val Asn Leu Glu Lys Met Pro Thr Glu Gly
        530                 535                 540

Glu Asp Leu Lys Leu Ser Cys Thr Val Asn Lys Phe Leu Tyr Arg Asp
545                 550                 555                 560

Val Thr Trp Ile Leu Leu Arg Thr Val Asn Asn Arg Thr Met His Tyr
                565                 570                 575

Ser Ile Ser Lys Gln Lys Met Ala Ile Thr Lys Glu His Ser Ile Thr
            580                 585                 590

Leu Asn Leu Thr Ile Met Asn Val Ser Leu Gln Asp Ser Gly Thr Tyr
        595                 600                 605

Ala Cys Arg Ala Arg Asn Val Tyr Thr Gly Glu Glu Ile Leu Gln Lys
    610                 615                 620

Lys Glu Ile Thr Ile Arg Asp Gln Glu Ala Pro Tyr Leu Leu Arg Asn
625                 630                 635                 640

Leu Ser Asp His Thr Val Ala Ile Ser Ser Thr Thr Leu Asp Cys
                645                 650                 655

His Ala Asn Gly Val Pro Glu Pro Gln Ile Thr Trp Phe Lys Asn Asn
            660                 665                 670

His Lys Ile Gln Gln Glu Pro Gly Ile Ile Leu Gly Pro Gly Ser Ser
        675                 680                 685

Thr Leu Phe Ile Glu Arg Val Thr Glu Glu Asp Glu Gly Val Tyr His
    690                 695                 700

Cys Lys Ala Thr Asn Gln Lys Gly Ser Val Glu Ser Ser Ala Tyr Leu
705                 710                 715                 720

Thr Val Gln Gly Thr Ser Asp Lys Ser Asn Leu Glu Leu Ile Thr Leu
                725                 730                 735

Thr Cys Thr Cys Val Ala Ala Thr Leu Phe Trp Leu Leu Leu Thr Leu
            740                 745                 750

Phe Ile Arg Lys Met Lys Arg Ser Ser Ser Glu Ile Lys Thr Asp Tyr
        755                 760                 765

Leu Ser Ile Ile Met Asp Pro Asp Glu Val Pro Leu Asp Glu Gln Cys
    770                 775                 780

Glu Arg Leu Pro Tyr Asp Ala Ser Lys Trp Glu Phe Ala Arg Glu Arg
785                 790                 795                 800

Leu Lys Leu Gly Lys Ser Leu Gly Arg Gly Ala Phe Gly Lys Val Val
                805                 810                 815

Gln Ala Ser Ala Phe Gly Ile Lys Lys Ser Pro Thr Cys Arg Thr Val
            820                 825                 830

Ala Val Lys Met Leu Lys Glu Gly Ala Thr Ala Ser Glu Tyr Lys Ala
        835                 840                 845

Leu Met Thr Glu Leu Lys Ile Leu Thr His Ile Gly His His Leu Asn
    850                 855                 860

Val Val Asn Leu Leu Gly Ala Cys Thr Lys Gln Gly Gly Pro Leu Met
865                 870                 875                 880

Val Ile Val Glu Tyr Cys Lys Tyr Gly Asn Leu Ser Asn Tyr Leu Lys
                885                 890                 895

Ser Lys Arg Asp Leu Phe Phe Leu Asn Lys Asp Ala Ala Leu His Met
            900                 905                 910

Glu Pro Lys Lys Glu Lys Met Glu Pro Gly Leu Glu Gln Gly Lys Lys
        915                 920                 925

Pro Arg Leu Asp Ser Val Thr Ser Ser Glu Ser Phe Ala Ser Ser Gly

-continued

```
                930             935             940
    Phe Gln Glu Asp Lys Ser Leu Ser Asp Val Glu Glu Glu Asp Ser
    945                 950             955             960

Asp Gly Phe Tyr Lys Glu Pro Ile Thr Met Glu Asp Leu Ile Ser Tyr
                    965             970             975

Ser Phe Gln Val Ala Arg Gly Met Glu Phe Leu Ser Ser Arg Lys Cys
                980             985             990

Ile His Arg Asp Leu Ala Ala Arg Asn Ile Leu Leu Ser Glu Asn Asn
            995                 1000            1005

Val Val Lys Ile Cys Asp Phe Gly Leu Ala Arg Asp Ile Tyr Lys
        1010            1015            1020

Asn Pro Asp Tyr Val Arg Lys Gly Asp Thr Arg Leu Pro Leu Lys
        1025            1030            1035

Trp Met Ala Pro Glu Ser Ile Phe Asp Lys Ile Tyr Ser Thr Lys
        1040            1045            1050

Ser Asp Val Trp Ser Tyr Gly Val Leu Leu Trp Glu Ile Phe Ser
        1055            1060            1065

Leu Gly Gly Ser Pro Tyr Pro Gly Val Gln Met Asp Glu Asp Phe
        1070            1075            1080

Cys Ser Arg Leu Arg Glu Gly Met Arg Met Arg Ala Pro Glu Tyr
        1085            1090            1095

Ser Thr Pro Glu Ile Tyr Gln Ile Met Leu Asp Cys Trp His Arg
        1100            1105            1110

Asp Pro Lys Glu Arg Pro Arg Phe Ala Glu Leu Val Glu Lys Leu
        1115            1120            1125

Gly Asp Leu Leu Gln Ala Asn Val Gln Gln Asp Gly Lys Asp Tyr
        1130            1135            1140

Ile Pro Ile Asn Ala Ile Leu Thr Gly Asn Ser Gly Phe Thr Tyr
        1145            1150            1155

Ser Thr Pro Ala Phe Ser Glu Asp Phe Phe Lys Glu Ser Ile Ser
        1160            1165            1170

Ala Pro Lys Phe Asn Ser Gly Ser Ser Asp Asp Val Arg Tyr Val
        1175            1180            1185

Asn Ala Phe Lys Phe Met Ser Leu Glu Arg Ile Lys Thr Phe Glu
        1190            1195            1200

Glu Leu Leu Pro Asn Ala Thr Ser Met Phe Asp Asp Tyr Gln Gly
        1205            1210            1215

Asp Ser Ser Thr Leu Leu Ala Ser Pro Met Leu Lys Arg Phe Thr
        1220            1225            1230

Trp Thr Asp Ser Lys Pro Lys Ala Ser Leu Lys Ile Asp Leu Arg
        1235            1240            1245

Val Thr Ser Lys Ser Lys Glu Ser Gly Leu Ser Asp Val Ser Arg
        1250            1255            1260

Pro Ser Phe Cys His Ser Ser Cys Gly His Val Ser Glu Gly Lys
        1265            1270            1275

Arg Arg Phe Thr Tyr Asp His Ala Glu Leu Glu Arg Lys Ile Ala
        1280            1285            1290

Cys Cys Ser Pro Pro Pro Asp Tyr Asn Ser Val Val Leu Tyr Ser
        1295            1300            1305

Thr Pro Pro Ile
        1310
```

METHODS AND COMPOSITIONS RELATING TO LUNG REPAIR

CROSS-REFERENCE TO RELATED APPLICATIONS

This application is a 35 U.S.C. § 371 National Phase Entry Application of International Application No. PCT/US2019/014867 filed Jan. 24, 2019, which designates the U.S. and claims benefit under 35 U.S.C. § 119 (e) of U.S. Provisional Application No. 62/646,493 filed Mar. 22, 2018, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Jan. 24, 2019, is named 701039-090440WOPT_SL.txt and is 87,789 bytes in size.

TECHNICAL FIELD

The technology described herein relates to methods of inducing growth and/or repair of lung tissue.

BACKGROUND

Vascular endothelial growth factor (VEGF) is a key regulator of angiogenesis and tissue growth. Previously, the soluble VEGF receptor (sFlt1) has been shown to deplete circulating VEGF, which provides inhibition of tumor growth and inhibition of liver regeneration. However, as shown herein, sFlt1 acts in a surprising and unexpected manner in lung tissue growth and repair, which directly contrasts with the activity previously described in tumors and liver.

SUMMARY

As described herein, the inventors have surprisingly found that, in the context of lung tissue growth and repair, sFlt1 acts to increase the rate of tissue growth and repair. This activity is directly opposed to the activity sFlt1 exhibits in other tissues, where it functions to inhibit VEGF.

In one aspect of any of the embodiments, described herein is a method of inducing growth and/or repair of lung tissue, the method comprising contacting the lung tissue with an agonist of sFlt1-Hif signalling. In one aspect of any of the embodiments, described herein is a method of inducing growth and/or repair of lung tissue in a subject in need thereof, the method comprising administering a therapeutically effective amount of an agonist of sFlt1-Hif signalling to the subject.

In some embodiments of any of the aspects, the growth and/or repair of lung tissue is compensatory lung growth. In some embodiments of any of the aspects, the subject is a subject with severe pulmonary hypoplasia; hypoplastic lung disease; congenital diaphragmatic hernia; bronchopulmonary dysplasia; emphysema; a disease with deficient alveolar count; alveolar capillary dysplasia; or who has undergone a pneumonectomy. In some embodiments of any of the aspects, the subject is not diagnosed with or in need of treatment for an inflammatory condition.

In some embodiments of any of the aspects, the agonist of sFlt1-Hif signaling is sFlt1 polypeptide. In some embodiments of any of the aspects, the sFlt1 polypeptide is a polypeptide comprising the sequence of one of SEQ ID Nos: 2-13. In some embodiments of any of the aspects, the sFlt1 polypeptide is a polypeptide comprising a sequence at least 95% identical to the sequence of one of SEQ ID Nos: 2-13 and retaining the activity of a polypeptide of SEQ ID Nos: 2-13.

In some embodiments of any of the aspects, the agonist further comprises an Fc domain conjugated to the sFlt1 polypeptide. In some embodiments of any of the aspects, the agonist is administered to the airway. In some embodiments of any of the aspects, the agonist is administered intravenously. In some embodiments of any of the aspects, the agonist is administered topically.

In some embodiments of any of the aspects, the agonist is administered at a dose of from about 5 mcg/kg to about 50 mcg/kg. In some embodiments of any of the aspects, the agonist is administered at a dose of about 20 mcg/kg.

In some embodiments of any of the aspects, the agonist of sFlt1-Hif signaling is an agonist of HIF1σ; HIF1β; and/or HIF2σ. In some embodiments of any of the aspects, the agonist is a HIF1σ; HIF1β; and/or HIF2σ polypeptide and/or a nucleic acid encoding said polypeptide. In some embodiments of any of the aspects, the agonist is a HIF Prolyl hydroxylase antagonist. In some embodiments of any of the aspects, the HIF Prolyl hydroxylase antagonist is JTZ-951; FG-4592; GSK1278863; FG-4592; or MK-8617.

In some embodiments of any of the aspects, endogenous VEGF levels are increased in the lung tissue and/or subject. In some embodiments of any of the aspects, the method results in higher lung volume, increased inspiratory capacity, increased exercise capacity, and/or increased pulmonary compliance.

DETAILED DESCRIPTION

Figure 1:
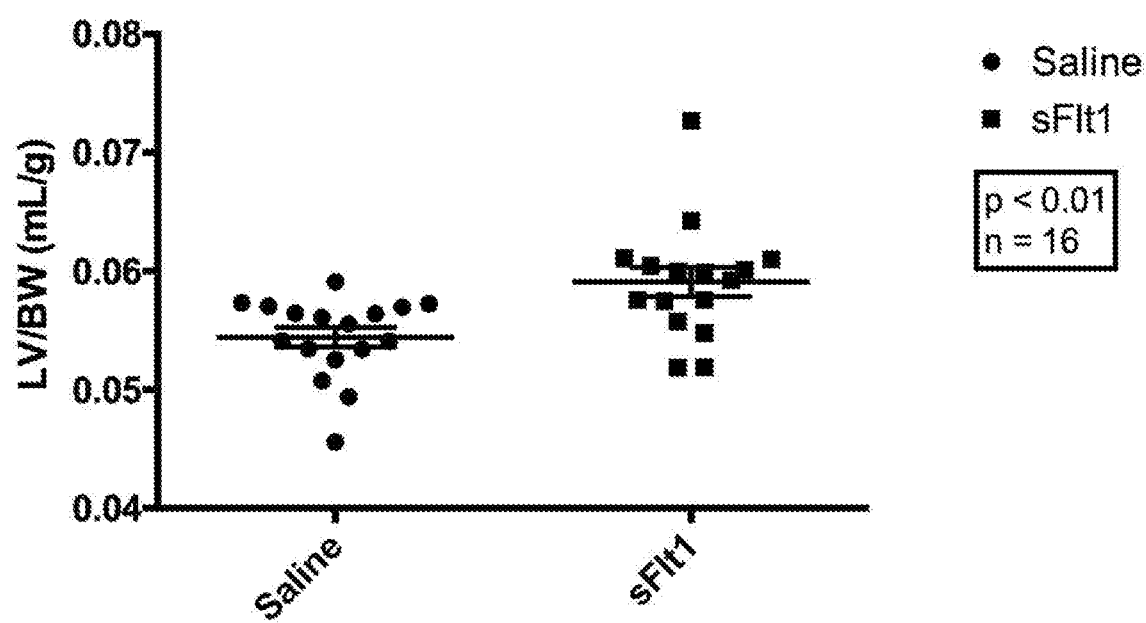
FIG. 1 depicts a graph demonstrating that sFlt1 increases lung volume on post-operative day 4. LV/BW: lung volume/body weight.
Figure 2:
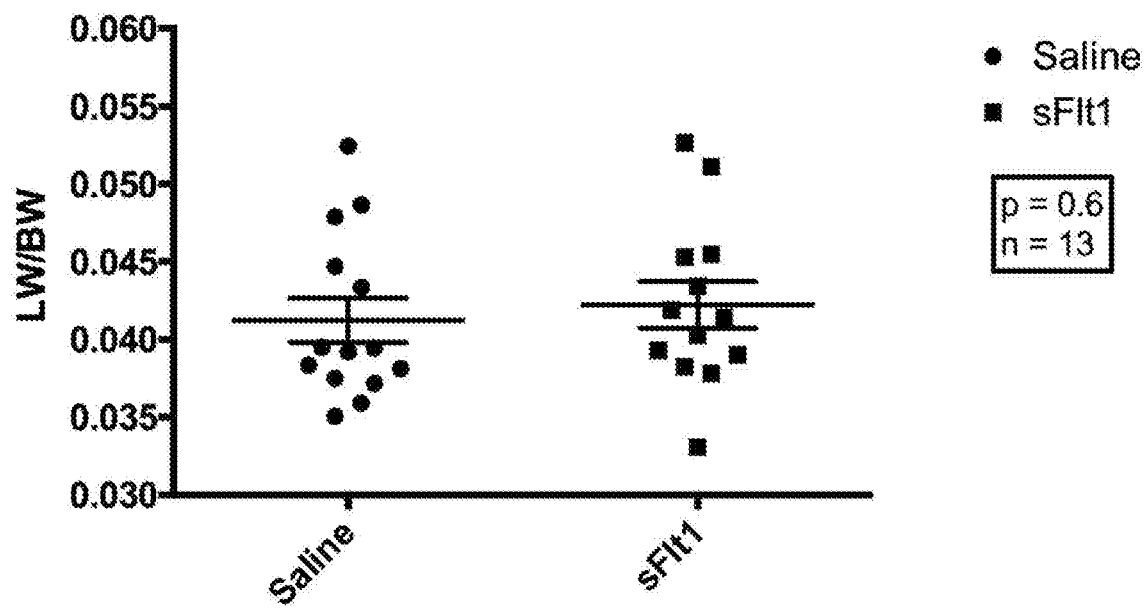
FIG. 2 depicts graphs demonstrating that sFlt1 does not change the organ mass of liver (top) and spleen (bottom). LW/BW: liver weight/body weight, SW/BW: spleen weight/body weight.
Figure 2:
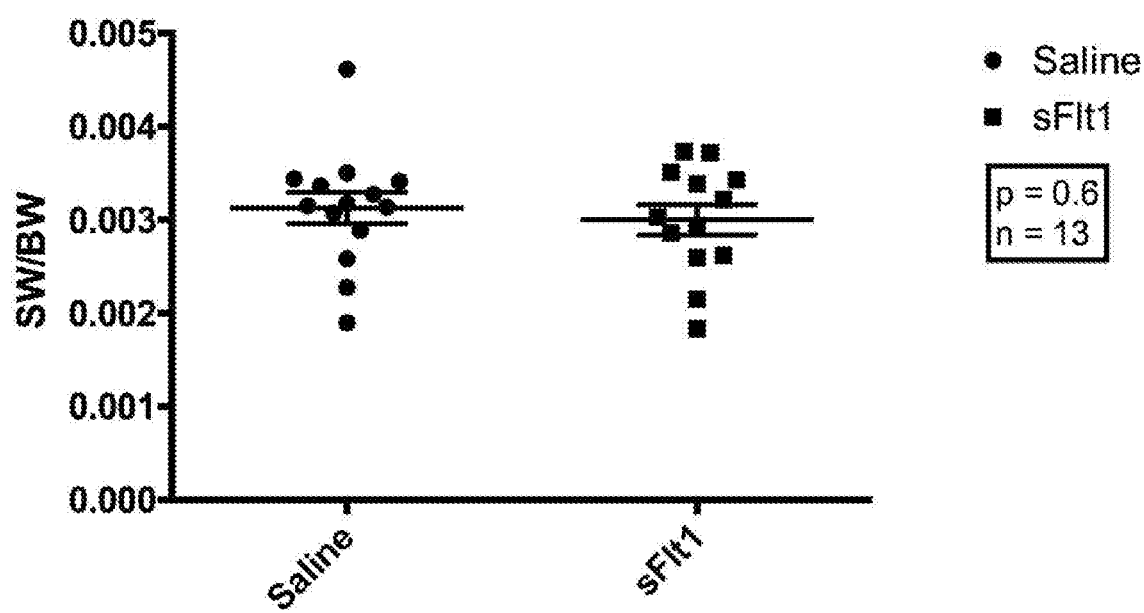
Figure 3:
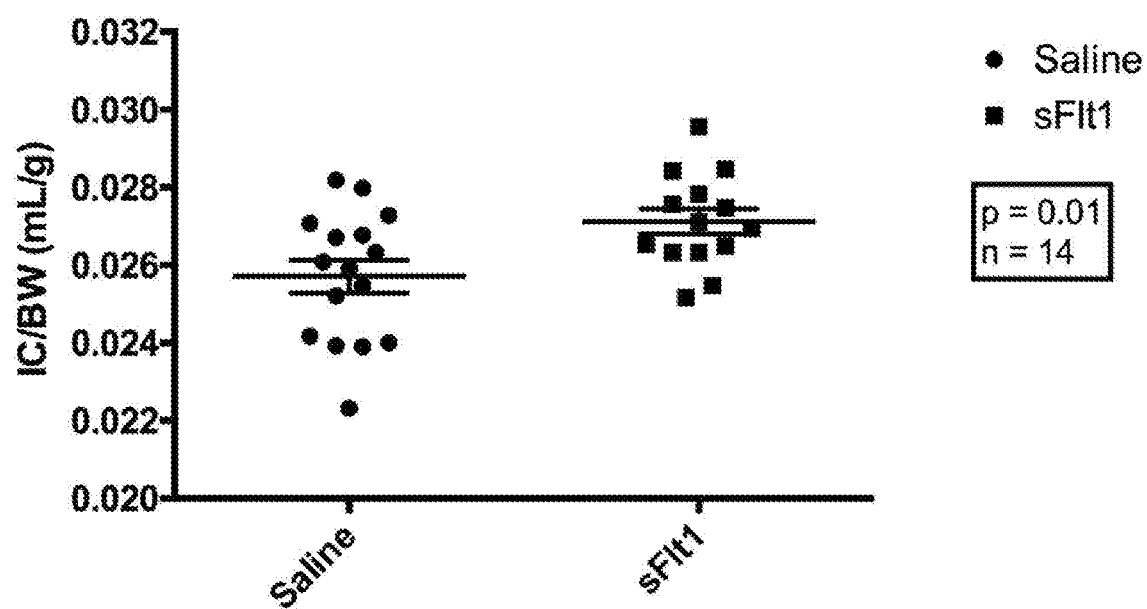
FIG. 3 depicts a graph demonstrating that sFlt1 increases inspiratory capacity on post-operative day 4. IC/BW: inspiratory capacity/body weight.
Figure 4:
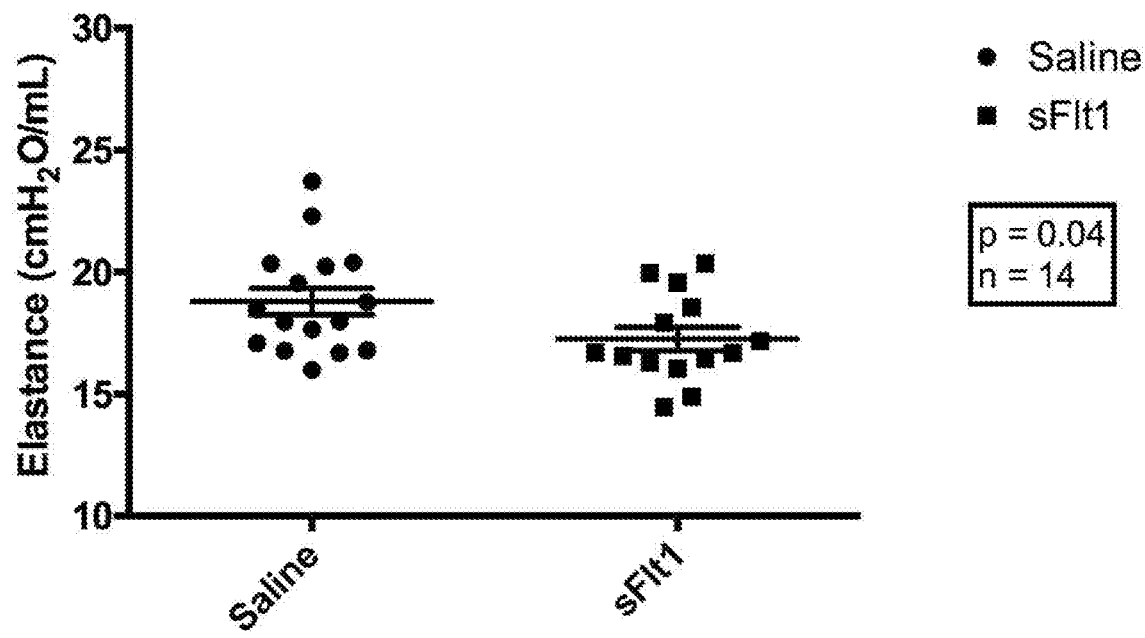
FIG. 4 depicts graphs demonstrating that sFlt1 improves pulmonary elastance (top) and compliance (bottom) on post-operative day 4.
Figure 4:
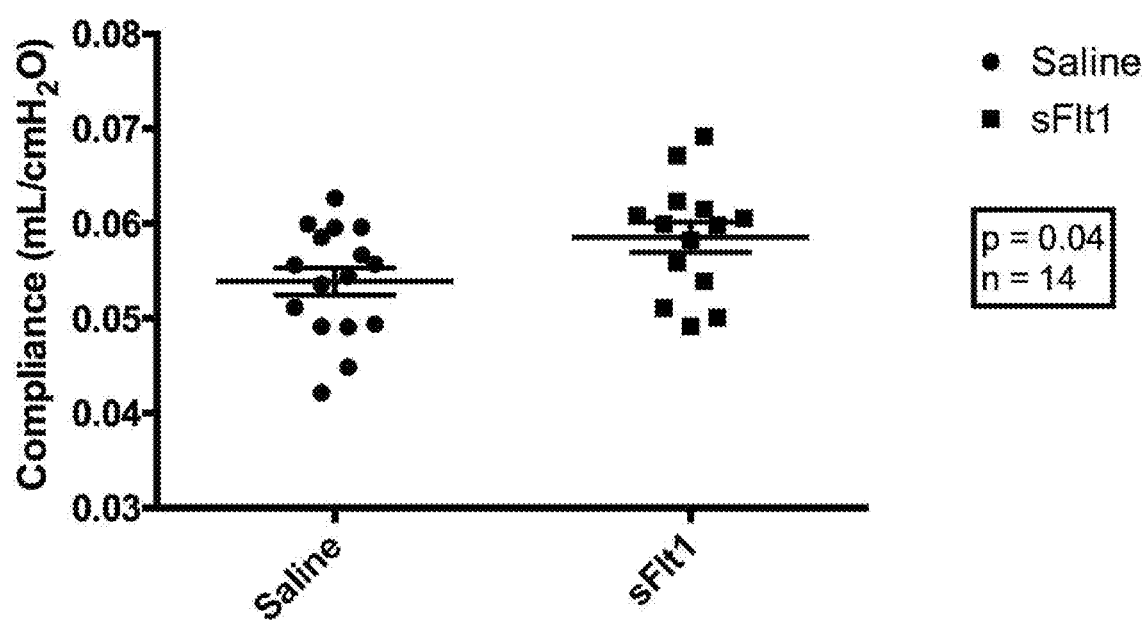
Figure 5:
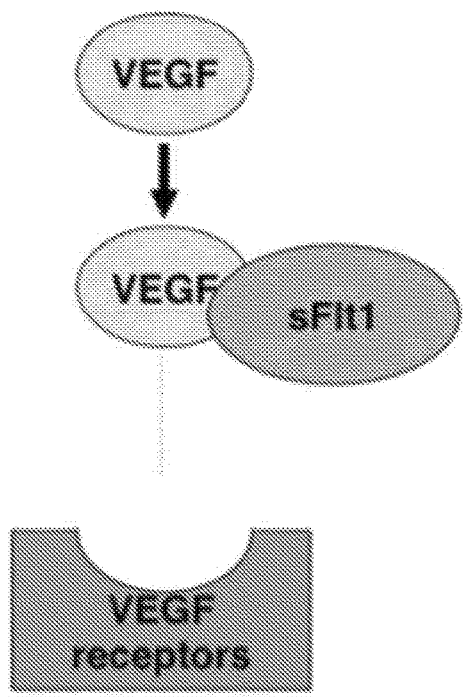
FIG. 5 depicts a diagram of signaling pathway activity.
Figure 5:
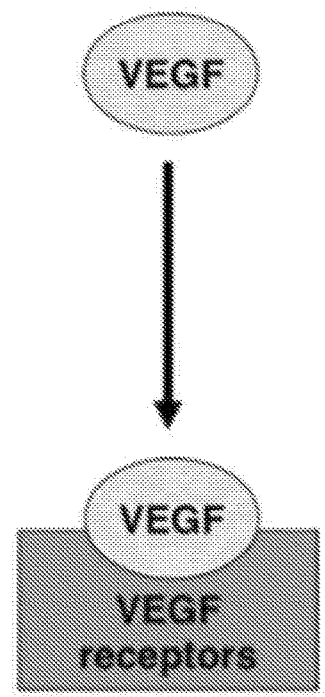

As demonstrated herein, sFlt1 acts to increase lung tissue growth and/or repair, thereby improving lung volume, inspiratory capacity, pulmonary elastance, and/or pulmonary compliance in damaged lung tissue. Also provided herein is evidence that this effect functions through the sFlt1-Hif signaling network. Accordingly, in one aspect of any of the embodiments, described herein is a method of inducing growth and/or repair of lung tissue, the method comprising contacting the lung tissue with an agonist of sFlt1-Hif signalling. In one aspect of any of the embodiments, described herein is a method of inducing growth and/or repair of lung tissue in a subject in need thereof, the method comprising administering a therapeutically effective amount of an agonist of sFlt1-Hif signalling to the subject.

Inducing growth and/or repair of lung tissue can comprise any increase in generation of new lung tissue, growth and/or expansion of existing lung tissue, or decrease in the degree or extent of lung tissue damage (e.g., scarring, fibrosis, hypoplasia, or the like). Growth and/or repair of lung tissue can be measured or determined histologically, or by assaying one or more functional measures of lung tissue performance, e.g., as described in the Examples herein. In some embodiments of any of the aspects, an increase in growth and/or repair of lung tissue can be a higher lung volume, an increase in inspiratory capacity, an increase in exercise capacity, and/or an increase in pulmonary compliance.

As used herein, the term "agonist" refers to an agent which increases the expression and/or activity of the target by at least 10% or more, e.g. by 10% or more, 50% or more, 100% or more, 200% or more, 500% or more, or 1000% or more. The efficacy of an agonist of, for example, sFlt1, e.g. its ability to increase the level and/or activity of sFlt1 can be determined, e.g. by measuring the level of an expression product of sFlt1 and/or the activity of sFlt1. Methods for measuring the level of a given mRNA and/or polypeptide are known to one of skill in the art, e.g. RTPCR with primers can be used to determine the level of RNA, and Western blotting with an antibody can be used to determine the level of a polypeptide. Suitable primers for a given target are readily identified by one of skill in the art, e.g., using software widely available for this purpose (e.g., Primer3 or PrimerBank, which are both available on the world wide web). Non-limiting examples of antibodies to sFlt1 are commercially available, e.g., Cat. No. sc-316 from Santa Cruz Biotechnology (Dallas, TX). Assays for measuring the activity of sFlt1, e.g. the level of lung tissue growth/repair and/or the level of free or circulating VEGF are described in the Examples herein.

Non-limiting examples of agonists of a given polypeptide target, e.g., sFlt1, can include the target polypeptides or variants or functional fragments thereof and nucleic acids encoding the polypeptide or variants or functional fragments thereof. In some embodiments of any of the aspects, the agonist of Flt1, is an sFlt1 polypeptide or variants or functional fragment thereof and/or a nucleic acid encoding the polypeptide or variant or functional fragment thereof.

As used herein, "sFlt1" or "soluble FMS-like tyrosine kinase 1" refers to a soluble variant of the VEGF receptor encoded by the Flt1 gene. Sequences for sFlt1 are known for a number of species, e.g., human sFlt1 (the Flt1 NCBI Gene ID is 2321) mRNA sequences (e.g., NM_001159920.1 (SEQ ID NO: 1) and polypeptide sequences (e.g., NP_001153392.1 (SEQ ID NO: 2) and SEQ ID NO: 4) as well as murine sFlt1 polypeptide sequences (e.g., SEQ ID NO: 3). An sFlt1 polypeptide does not comprise a transmembrane domain, e.g., a Flt1 transmembrane domain.

In some embodiments of any of the aspects, the agonist of, e.g. sFlt1 can be a sFlt1 polypeptide. In some embodiments of any of the aspects, the polypeptide agonist can be an engineered and/or recombinant polypeptide. In some embodiments of any of the aspects, the polypeptide agonist can be a nucleic acid encoding a polypeptide, e.g. a functional fragment thereof. In some embodiments of any of the aspects, the nucleic acid can be comprised by a vector.

In some embodiments of any of the aspects, an sFlt1 agonist can be a polypeptide comprising the sequence of a human sFlt1 polypeptide, e.g., SEQ ID NO: 2 or SEQ ID NO: 4. In some embodiments of any of the aspects, an sFlt1 agonist can be a polypeptide consisting essentially of the sequence of a human sFlt1 polypeptide, e.g., SEQ ID NO: 2 or SEQ ID NO: 4. In some embodiments of any of the aspects, an sFlt1 agonist can be a polypeptide consisting of the sequence of a human sFlt1 polypeptide, e.g., SEQ ID NO: 2 or SEQ ID NO: 4.

In some embodiments of any of the aspects, an sFlt1 agonist can be a polypeptide comprising the sequence of SEQ ID NO: 2 or SEQ ID NO: 4. In some embodiments of any of the aspects, an sFlt1 agonist can be a polypeptide consisting essentially of the sequence of SEQ ID NO: 2 or SEQ ID NO: 4. In some embodiments of any of the aspects, an sFlt1 agonist can be a polypeptide consisting of the sequence of SEQ ID NO: 2 or SEQ ID NO: 4.

In some embodiments of any of the aspects, a sFlt1 agonist can be a nucleic acid comprising a sequence which encodes a human sFlt1 polypeptide, e.g., SEQ ID NO: 1. In some embodiments of any of the aspects, a sFlt1 agonist can be a nucleic acid comprising a sequence which encodes a polypeptide of SEQ ID NO: 2 or 4.

```
Murine sFlt1
                                         SEQ ID NO: 3
  sklk vpelslkgtq hvmqagqtlf lkcrgeaahs wslpttvsqe dkrlsitpps acgrdnrqfc stltldtaqa nhtglytcry lptstskkkk aessiyifvs dagspfiemh tdipklvhmt egrqliiper vtspnvtvtl kkfpfdtltp dgqritwdsr rgfiianaty keigllncea tvnghlyqtn ylthrqtnti ldvqirppsp vrllhgqtlv lnctatteln trvqmswnyp gkatkrasir qridrshshn nvfhsvlkin nvesrdkgly tcrvksgssf qsfntsvhvy ekgfisvkhr kqpvqettag rrsyrlsmkv kafpspeivw lkdgspatlk sarylvhgys liikdvtted agdytillgi kqsrlfknlt atlivnvkpq iyeksvsslp spplyplgsr qvltctvygi prptitwlwh pchhnhsker ydfctenees fildpssnlg nriesisqrm tviegtnktv stlvvadsqt pgiyscrafn kigtvernik fyvtdvpngf hvslekmpae gedlklscvv
```

```
                                                            -continued
nkflyrditw illrtvnnrt mhhsiskqkm attqdysitl
nlviknvsle dsgtyacrar niytgedilr ktevlvrdse
aphllqnlsd yevsisgstt ldcqargvpa pqitwfknnh
kiqqepgiil gpgnstlfie rvteedegvy rcratnqkga
vesaayltvq gtsdksnle SEQ ID NO: 4
sklk dpelslkgtq himqagqtlh lqcrgeaahk
wslpemvske serlsitksa cgrngkqfcs tltlntaqan
htgfysckyl avptskkket esaiyifisd tgrpfvemys
eipeiihmte grelvipcrv tspnitvtlk kfpldtlipd
gkriiwdsrk gfiisnatyk eiglltceat vnghlyktny
lthrqtntii dvqistprpv kllrghtlvl nctattplnt
rvqmtwsypd eknkrasvrr ridqsnshan ifysvltidk
mqnkdkglyt crvrsgpsfk svntsvhiyd kafitvkhrk
qqvletvagk rsyrlsmkvk afpspevvwl kdglpateks
aryltrgysl iikdvteeda gnytillsik qsnvfknlta
tlivnvkpqi yekavssfpd palyplgsrq iltctaygip
```

```
                                                            -continued
qptikwfwhp cnhnhsearc dfcsnneesf ildadsnmgn
riesitqrma iiegknkmas tlvvadsris giyiciasnk
vgtvgrnisf yitdvpngfh vnlekmpteg edlklsctvn
kflyrdvtwi lirtvnnrtm hysiskqkma itkehsitln
ltimnvslqd sgtyacrarn vytgeeilqk keitir
```

In some embodiments of any of the aspects, an sFlt1 agonist can be a polypeptide comprising the sequence of SEQ ID NOs: 5, 6, 7, 8, 9, 10, 11, 12, or 13. In some embodiments of any of the aspects, an sFlt1 agonist can be a polypeptide consisting essentially of the sequence of SEQ ID NOs: 5, 6, 7, 8, 9, 10, 11, 12, or 13. In some embodiments of any of the aspects, an sFlt1 agonist can be a polypeptide consisting of the sequence of SEQ ID NOs: 5, 6, 7, 8, 9, 10, 11, 12, or 13. In some embodiments of any of the aspects, a sFlt1 agonist can be a nucleic acid comprising a sequence which encodes a sFlt1 polypeptide, e.g., a polypeptide comprising the sequence of SEQ ID Nos: 5, 6, 7, 8, 9, 10, 11, 12, or 13.

In some embodiments of any of the aspects, an sFlt1 agonist can be a polypeptide comprising the sequence with at least 80%, at least 85%, at least 90%, at least 95%, or at least 98% identity to one of SEQ ID NOs: 2-13 and which retains the VEGF-binding activity of a polypeptide of one of SEQ ID Nos: 2-13.

```
                                                            SEQ ID NO: 5
mvsywdtgvl lcallsclll tgsssgsklk dpelslkgtq himqagqtlh lqcrgeaahk
wslpemvske serlsitksa cgrngkqfcs tltlntaqan htgfysckyl avptskkket
esaiyifisd tgrpfvemys eipeiihmte grelvipcrv tspnitvtlk kfpldtlipd
gkriiwdsrk gfiisnatyk eiglltceat vnghlyktny lthrqtntii dvqistprpv
kllrghtlvl nctattplnt rvqmtwsypd eknkrasvrr ridqsnshan ifysvltidk
mqnkdkglyt crvrsgpsfk svntsvhiyd kafitvkhrk qqvletvagk rsyrlsmkvk
afpspevvwl kdglpateks aryltrgysl iikdvteeda gnytillsik qsnvfknlta
tlivnvkpqi yekavssfpd palyplgsrq iltctaygip qptikwfwhp cnhnhsearc
dfcsnneesf ildadsnmgn riesitqrma iiegknkmas tlvvadsris giyiciasnk
vgtvgrnisf yitdvpngfh vnlekmpteg edlklsctvn kflyrdvtwi llrtvnnrtm
hysiskqkma itkehsitln ltimnvslqd sgtyacrarn vytgeeilqk keitirdqea
pyllrnlsdh tvaisssttl dchangvpep qitwfknnhk iqqepelyts tspsssssssp
lssssssss sss
                                                            SEQ ID NO: 6
sklk dpelslkgtq himqagqtlh lqcrgeaahk
wslpemvske serlsitksa cgrngkqfcs tltlntaqan htgfysckyl avptskkket
esaiyifisd tgrpfvemys eipeiihmte grelvipcrv tspnitvtlk kfpldtlipd
gkriiwdsrk gfiisnatyk eiglltceat vnghlyktny lthrqtntii dvqistprpv
kllrghtlvl nctattplnt rvqmtwsypd eknkrasvrr ridqsnshan ifysvltidk
mqnkdkglyt crvrsgpsfk svntsvhiyd kafitvkhrk qqvletvagk rsyrlsmkvk
afpspevvwl kdglpateks aryltrgysl iikdvteeda gnytillsik qsnvfknlta
tlivnvkpqi yekavssfpd palyplgsrq iltctaygip qptikwfwhp cnhnhsearc
dfcsnneesf ildadsnmgn riesitqrma iiegknkmas tlvvadsris giyiciasnk
```

-continued vgtvgrnisf yitdvpngfh vnlekmpteg edlklsctvn kflyrdvtwi llrtvnnrtm hysiskqkma itkehsitln ltimnvslqd sgtyacrarn vytgeeilqk keitirdqea iqqep

SEQ ID NO: 7 sklk dpelslkgtq himqagqtlh lqcrgeaahk wslpemvske serlsitksa cgrngkqfcs tltintaqan htgfysckyl avptskkket esaiyifisd tgrpfvemys eipeiihmte grelvipery tspnitvtlk kfpldtlipd gkriiwdsrk gfiisnatyk eiglltceat vnghlyktny lthrqtntii dvqistprpv kllrghtivl nctattpint rvqmtwsypd eknkrasvrr ridqsnshan ifysvltidk mqnkdkglyt crvrsgpsfk svntsvhiyd kafitvkhrk qqvletvagk rsyrlsmkvk afpspevvwl kdglpateks aryltrgysl iikdvteeda gnytillsik qsnvfknita tlivnvkpqi yekayssfpd palyplgsrq iltctaygip qptikwfwhp cnhnhsearc dfcsnneesf ildadsnmgn riesitqrma iiegknkmas tivvadsris giyiciasnk vgtvgrnisf yitdvpngfh vnlekmpteg edlklsctvn kflyrdvtwi llrtynnrtm hysiskqkma itkehsitln ltimnvslqd sgtyacrarn vytgeeilqk keitirdqea iqqepelyts tspsssssp lssssssss sss

SEQ ID NO: 8 mvsywdtgvl lcallsclll tgsssgsklk dpelslkgtq himqagqtlh lqcrgeaahk wslpemvske serlsitksa cgrngkqfcs tltlntaqan htgfysckyl avptskkket esaiyifisd tgrpfvemys eipeiihmte grelvipcrv tspnitvtlk kfpldtlipd gkriiwdsrk gfiisnatyk eiglltceat vnghlyktny lthrqtntii dvqistprpv kllrghtlvl nctattplnt rvqmtwsypd eknkrasvrr ridqsnshan ifysvltidk mqnkdkglyt crvrsgpsfk svntsvhiyd kafitvkhrk qqvletvagk rsyrlsmkvk afpspevvwl kdglpateks aryltrgysl iikdvteeda gnytillsik qsnvfknlta tlivnvkpqi yekavssfpd palyplgsrq iltctaygip qptikwfwhp cnhnhsearc dfcsnneesf ildadsnmgn riesitqrma iiegknklpp anssfmlppt sfssnyfhfl p

SEQ ID NO: 9 sklk dpelslkgtq himqagqtlh lqcrgeaahk wslpemvske serlsitksa cgrngkqfcs tltlntaqan htgfysckyl avptskkket esaiyifisd tgrpfvemys eipeiihmte grelvipcrv tspnitvtlk kfpldtlipd gkriiwdsrk gfiisnatyk eiglltceat vnghlyktny lthrqtntii dvqistprpv kllrghtlvl nctattplnt rvqmtwsypd eknkrasvrr ridqsnshan ifysvltidk mqnkdkglyt crvrsgpsfk svntsvhiyd kafitvkhrk qqvletvagk rsyrlsmkvk afpspevvwl kdglpateks aryltrgysl iikdvteeda gnytillsik qsnvflnlta tlivnvkpqi yekavssfpd palyplgsrq iltctaygip qptikwfwhp cnhnhsearc dfcsnneesf ildadsnmgn riesitqrma iiegknk

SEQ ID NO: 10 sklk dpelslkgtq himqagqtlh lqcrgeaahk wslpemvske serlsitksa cgrngkqfcs tltlntaqan htgfysckyl avptskkket esaiyifisd tgrpfvemys eipeiihmte grelvipery tspnitvtlk kfpldtlipd gkriiwdsrk gfiisnatyk eiglltceat vnghlyktny lthrqtntii dvqistprpv kllrghtivl nctattpint rvqmtwsypd eknkrasvrr ridqsnshan ifysvltidk -continued

```
mqnkdkglyt crvrsgpsfk svntsvhiyd kafitvkhrk qqvletvagk rsyrlsmkvk afpspevvwl kdglpateks aryltrgysl iikdvteeda gnytillsik qsnvfknita tlivnvkpqi yekayssfpd palyplgsrq iltctaygip qptikwfwhp cnhnhsearc dfcsnneesf ildadsnmgn riesitqrma iiegknklpp anssfmlppt sfssnyfhfl p
```

SEQ ID NO: 11
```
mvsywdtgvl lcallsclll tgsssgsklk dpelslkgtq himqagqtlh lqcrgeaahk wslpemvske serlsitksa cgrngkqfcs tltlntaqan htgfysckyl avptskkket esaiyifisd tgrpfvemys eipeiihmte grelvipcrv tspnitvtlk kfpldtlipd gkriiwdsrk gfiisnatyk eiglltceat vnghlyktny lthrqtntii dvqistprpv kllrghtlvl nctattplnt rvqmtwsypd eknkrasvrr ridqsnshan ifysvltidk mqnkdkglyt crvrsgpsfk svntsvhiyd kafitvkhrk qqvletvagk rsyrlsmkvk afpspevvwl kdglpateks aryltrgysl iikdvteeda gnytillsik qsnvfknlta tlivnvkpqi yekavssfpd palyplgsrq iltctaygip qptikwfwhp cnhnhsearc dfcsnneesf ildadsnmgn riesitqrma iiegknkmas tlvvadsris giyiciasnk vgtvgrnisf yitdvpngfh vnlekmpteg edlklsctvn kflyrdvtwi llrtvnnrtm hysiskqkma itkehsitln ltimnvslqd sgtyacrarn vytgeeilqk keitirdqea pyllrnlsdh tvaisssttl dchangvpep qitwfknnhk iqqepgiilg pgsstlfier vteedegvyh ckatnqkgsv essayltvqg tsdksnleli tltctcvaat lfwilltlfi rkmkrsssei ktdylsiimd pdevpldeqc erlpydaskw efarerlklg kslgrgafgk vvqasafgik ksptcrtvav kmlkegatas eykalmtelk ilthighhln vvnllgactk qggplmvive yckygnlsny lkskrdlffl nkdaalhmep kkekmepgle qgkkprldsv tssesfassg fqedkslsdv eeeedsdgfy kepitmedli sysfqvargm eflssrkcih rdlaarnill sennvvkicd fglardiykn pdyvrkgdtr lplkwmapes ifdkiystks dvwsygvllw eifslggspy pgvqmdedfc srlregmrmr apeystpeiy qimldcwhrd pkerprfael veklgdllqa nvqqdgkdyi pinailtgns gftystpafs edffkesisa pkfnsgssdd vryvnafldm sleriktfee llpnatsmfd dyqgdsstll aspmlkrftw tdskpkaslk idlrvtsksk esglsdvsrp sfchsscghv segkrrftyd haelerkiac cspppdynsv vlystppi
```

SEQ ID NO: 12
```
mvsywdtgvl lcallsclll tgsssgsklk dpelslkgtq himqagqtlh lqcrgeaahk wslpemvske serlsitksa cgrngkqfcs tltlntaqan htgfysckyl avptskkket esaiyifisd tgrpfvemys eipeiihmte grelvipcrv tspnitvtlk kfpldtlipd gkriiwdsrk gfiisnatyk eiglltceat vnghlyktny lthrqtntii dvqistprpv kllrghtlvl nctattplnt rvqmtwsypd eknkrasvrr ridqsnshan ifysvltidk mqnkdkglyt crvrsgpsfk svntsvhiyd kafitvkhrk qqvletvagk rsyrlsmkvk afpspevvwl kdglpateks aryltrgysl iikdvteeda gnytillsik qsnvfknlta tlivnvkpqi yekavssfpd palyplgsrq iltctaygip qptikwfwhp cnhnhsearc dfcsnneesf ildadsnmgn riesitqrma iiegknkmas tlvvadsris giyiciasnk vgtvgrnisf yitdvpngfh vnlekmpteg edlklsctvn kflyrdvtwi llrtvnnrtm hysiskqkma itkehsitln ltimnvslqd sgtyacrarn vytgeeilqk keitirdqea pyllrnlsdh tvaisssttl dchangvpep qitwfknnhk iqqepgiilg pgsstlfier vteedegvyh ckatnqkgsv essayltvqg tsdksnle
```

-continued

SEQ ID NO: 13

```
sklk dpelslkgtq himqagqtlh lqcrgeaahk wslpemvske serlsitksa cgrngkqfcs tltlntaqan htgfysckyl avptskkket esaiyifisd tgrpfvemys eipeiihmte grelvipcrv tspnitvtlk kfpldtlipd gkriiwdsrk gfiisnatyk eiglltceat vnghlyktny lthrqtntii dvqistprpv kllrghtlvl nctattplnt rvqmtwsypd eknkrasvrr ridqsnshan ifysvltidk mqnkdkglyt crvrsgpsfk svntsvhiyd kafitvkhrk qqvletvagk rsyrlsmkvk afpspevvwl kdglpateks aryltrgysl iikdvteeda gnytillsik qsnvfknlta tlivnvkpqi yekavssfpd palyplgsrq iltctaygip qptikwfwhp cnhnhsearc dfcsnneesf ildadsnmgn riesitqrma iiegknkmas tlvvadsris giyiciasnk vgtvgrnisf yitdvpngfh vnlekmpteg edlklsctvn kflyrdvtwi llrtvnnrtm hysiskqkma itkehsitln ltimnvslqd sgtyacrarn vytgeeilqk keitirdqea pyllrnlsdh tvaisssttl dchangvpep qitwfknnhk iqqepgiilg pgsstlfier vteedegvyh ckatnqkgsv essayltvqg tsdksnleli tltctcvaat lfwilltifi rkmkrsssei ktdylsiimd pdevpldeqc erlpydaskw efarerlklg kslgrgafgk vvqasafgik ksptcrtvav kmlkegatas eykalmtelk ilthighhln vvnllgactk qggplmvive yckygnlsny lkskrdlffl nkdaalhmep kkekmepgle qgkkprldsv tssesfassg fqedkslsdv eeeedsdgfy kepitmedli sysfqvargm eflssrkcih rdlaarnill sennvvkicd fglardiykn pdyvrkgdtr lplkwmapes ifdkiystks dvwsygvllw eifslggspy pgvqmdedfc srlregmrmr apeystpeiy qimldcwhrd pkerprfael veklgdllqa nvqqdgkdyi pinailtgns gftystpafs edffkesisa pkfnsgssdd vryvnafldm sleriktfee lipnatsmfd dyqgdsstll aspmlkrftw tdskpkaslk idlrvtsksk esglsdvsrp sfchsscghv segkrrftyd haelerkiac cspppdynsv vlystppi
```

In some embodiments of any of the aspects, the agonist of, e.g., sFlt1, can be a sFlt1 polypeptide, e.g., exogenous sFlt1 polypeptide. In some embodiments of any of the aspects, the target cell(s) and/or subject is contacted with and/or administered exogenous sFlt1 polypeptide, e.g., sFlt1 polypeptide is produced in vitro and/or synthesized and purified sFlt1 polypeptide is provided to the target cell(s) and/or subject.

In some embodiments of any of the aspects, the agonist of sFlt1 can comprise an sFlt1 polypeptide conjugated to an Fc domain polypeptide, e.g., to a human Fc domain, e.g., to extend the half-life of the agonist. Suitable Fc domain sequences are known in the art (e.g., Pro100-Lys330 of human IgG1).

In some embodiments of any of the aspects, the agonist of sFlt1 can be provided in a nanoparticle or in a topical formulation, e.g., with or without a carrier.

In some embodiments of any of the aspects, the agonist of, e.g., sFlt1, can be a nucleic acid encoding a polypeptide comprising the sequence of sFlt1 (or a variant or functional fragment thereof) and/or a vector comprising a nucleic acid encoding a polypeptide comprising the sequence of sFlt1 (or a variant or functional fragment thereof). A nucleic acid encoding a polypeptide can be, e.g., an RNA molecule, a plasmid, and/or an expression vector. In some embodiments of any of the aspects, the nucleic acid encoding a polypeptide can be an mRNA. In some embodiments of any of the aspects, the nucleic acid encoding a polypeptide can be a modified mRNA.

In some embodiments of any of the aspects, the agonist of, e.g., sFlt1, can be a nucleic acid encoding a sFlt1 polypeptide, e.g., exogenous and/or ectopic sFlt1 polypeptide. In some embodiments of any of the aspects, the target cell(s) and/or subject is contacted with and/or administered the nucleic acid encoding exogenous and/or ectopic sFlt1 polypeptide, e.g., the nucleic acid is transcribed and/or translated after the contacting or administering step to provide exogenous and/or ectopic sFlt1 to the target cell(s) and/or subject.

An agonist of sFlt1-Hif signaling is an agent which increases the expression and/or activity of sFlt1 or any of the Hif polypeptides that it signals through in controlling lung tissue growth/repair, e.g., HIF1σ; HIF1β; and/or HIF2σ. HIF-1 is a transcriptional complex comprising an alpha subunit and a beta subunit.

As used herein, "HIF1σ" or "hypoxia inducible factor 1 alpha subunit" refers to an alpha subunit of the HIF-1 transcriptional complex comprising a bHLH DNA-binding domain, an PAS heterodimerization domain, and a C-terminal recruitment domain. Sequences for HIF1σ are known for a number of species, e.g., human HIF1σ (NCBI Gene ID is 3091) mRNA sequences (NM_001243084.1; NM_001530.3; and NM_181054.2) and polypeptide sequences (NP_001230013.1; NP_001521.1; and NP_851397.1).

As used herein, "HIF1β", "hypoxia inducible factor 1 beta subunit", or "ARNT" refers to a beta subunit of the HIF-1 transcriptional complex which is an aryl hydrocarbon receptor nuclear translocator comprising a bHLH DNA-binding domain, an PAS heterodimerization domain, and a C-terminal recruitment domain. Sequences for HIF1β are known for a number of species, e.g., human HIF1β (NCBI Gene ID is 405) mRNA sequences (NM_001197325.1; NM_001286035.1; NM_001286036.1; NM_001350224.1; NM_001350225.1; NM_001350226.1; NM_001668.3; and NM_178427.2) and polypeptide sequences (NP_001184254.1; NP_001272964.1; NP_001272965.1; NP_001337153.1; NP_001337154.1; NP_001337155.1; NP_001659.1; and NP_848514.1).

As used herein, "HIF2σ", "EPAS1", or "hypoxia inducible factor 2 alpha subunit" refers to an alpha subunit of the HIF-1 transcriptional complex comprising a bHLH DNA-binding domain, an PAS heterodimerization domain, and a C-terminal recruitment domain. Sequences for HIF2σ are known for a number of species, e.g., human HIF2σ (NCBI Gene ID is 2034) mRNA sequences (NM_001430.4) and polypeptide sequences (NP_001421.2).

In some embodiments, the agonist of sFlt1 or the agonist of sFlt1-Hif signaling can be a small molecule, for example, a small molecule that inhibits the degradation of HIF, e.g., a HIF Prolyl hydroxylase antagonist. Non-limiting examples of such small molecules include JTZ-951 (PMID: 29259755), FG-4592 (PMID: 29153032), GSK1278863 (PMID: 28928122), FG-4592 (PMID: 28371815), and MK-8617 (PMID: 28002958). Suitable small molecules are further discussed in the art by, e.g., Gupta et al. Am J Kidney Dis 2017 69:815-826; which is incorporated by reference herein in its entirety.

In some embodiments of any of the aspects, the contacting or administering described herein causes levels of endogenous VEGF to be increased in the lung tissue and/or subject (e.g., in the circulation or lung of the subject). VEGF levels can be measured by one of skill in the art using, e.g., readily available immunological methods.

In some embodiments of any of the aspects described herein, the method comprises contacting lung tissue with an agent described herein. Contacting lung tissue can comprise contacting lung tissue maintained ex vivo, or comprise administering the agent to a subject such that at least a portion of the agent reaches the subject's lung tissue.

In some embodiments of any of the aspects, the methods described herein relate to treating a subject having or diagnosed as having severe pulmonary hyperplasia; hypoplastic lung disease; congenital diaphragmatic hernia; bronchopulmonary dysplasia; emphysema; a disease with deficient alveolar count; a deficient alveolar count; and/or alveolar capillary dysplasia with an agent described herein. In some embodiments of any of the aspects, the methods described herein relate to treating a subject who has undergone a pneumonectomy, e.g., a partial or complete pneumonectomy with an agent described herein. Subjects having one or more of these conditions, e.g, emphysema can be identified by a physician using current methods of diagnosing emphysema. Symptoms and/or complications of emphysema which characterize these conditions and aid in diagnosis are well known in the art and include but are not limited to, shortness of breath. Tests that may aid in a diagnosis of, e.g. emphysema include, but are not limited to, chest x-rays, CT scans, and lung function tests. A family history of emphysema or exposure to risk factors for emphysema (e.g. smoke exposure, pollution exposure, fume/dust exposure) can also aid in determining if a subject is likely to have emphysema or in making a diagnosis of emphysema.

In some embodiments of any of the aspects described herein, the subject is a subject who does not have or is not diagnosed as having an inflammatory disease or condition. In some embodiments of any of the aspects described herein, the subject is a subject who does not have or is not diagnosed as having a disease or condition which arises from or is exacerbated by inflammation. In some embodiments of any of the aspects described herein, the subject is a subject who does not have or is not diagnosed as having inflammation in their lung tissue.

The compositions and methods described herein can be administered to a subject having or diagnosed as having a condition described herein. In some embodiments of any of the aspects, the methods described herein comprise administering an effective amount of compositions described herein, e.g. an agonist of sFlt1-Hif signaling, to a subject in order to alleviate a symptom of a condition. As used herein, "alleviating a symptom" is ameliorating any condition or symptom associated with the condition. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to, oral, parenteral, intravenous, intramuscular, subcutaneous, transdermal, airway (aerosol), pulmonary, cutaneous, injection, or topical administration. Administration can be local or systemic.

The term "effective amount" as used herein refers to the amount of an agonist of sFlt1-Hif signalling needed to alleviate at least one or more symptom of the disease or disorder, and relates to a sufficient amount of pharmacological composition to provide the desired effect. The term "therapeutically effective amount" therefore refers to an amount of an agonist of sFlt1-Hif signalling that is sufficient to provide a particular growth and/or repair effect when administered to a typical subject. An effective amount as used herein, in various contexts, would also include an amount sufficient to delay the development of a symptom of the disease, alter the course of a symptom of the disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the agonist of sFlt1-Hif signalling, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for lung function and/or VEGF levels, among others. The dosage can be determined by a physician and adjusted, as necessary, to suit observed effects of the treatment.

In some embodiments of any of the aspects, the technology described herein relates to a pharmaceutical composition comprising an agonist of sFlt1-Hif signalling as described herein, and optionally a pharmaceutically acceptable carrier. In some embodiments of any of the aspects, the active ingredients of the pharmaceutical composition comprise an agonist of sFlt1-Hif signalling as described herein. In some embodiments of any of the aspects, the active ingredients of the pharmaceutical composition consist essentially of an agonist of sFlt1-Hif signalling as described herein. In some embodiments of any of the aspects, the active ingredients of the pharmaceutical composition consist of an agonist of sFlt1-Hif signalling as described herein. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments of any of the aspects, the carrier inhibits the degradation of the active agent, e.g. an agonist of sFlt1-Hif signalling as described herein.

In some embodiments of any of the aspects, the pharmaceutical composition comprising an agonist of sFlt1-Hif signalling as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an agonist of sFlt1-Hif signalling as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an agonist as disclosed herein can also be incorporated into the parenteral dosage forms of the disclosure, including conventional and controlled-release parenteral dosage forms.

Pharmaceutical compositions comprising an agonist of sFlt1-Hif signalling can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia PA (2005).

In some embodiments of any of the aspects, an agonist of sFlt1-Hif signalling described herein can be administered by inhalation, e.g., as a vapor or aerosol formulation or by nebulization. For use as aerosols, an agonist of sFlt1-Hif signalling described herein can be provided in solution or suspension may be packaged in a pressurized aerosol container together with suitable propellants, for example, hydrocarbon propellants like propane, butane, or isobutane with conventional adjuvants. An agonist of sFlt1-Hif signalling described herein can also be administered in a non-pressurized form such as in a nebulizer or atomizer. In some embodiments of any of the aspects, an agonist of sFlt1-Hif signalling can also be administered directly to the airways in the form of a dry powder, e.g., by use with an inhaler. Aerosols for the delivery to the respiratory tract are known in the art. See for example, Adjei, A. and Garren, J. Pharm. Res., 1: 565-569 (1990); Zanen, P. and Lamm, J.-W. J. Int. J. Pharm., 114: 111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140: 1317-1324 (1989)) and have potential for the systemic delivery of peptides and proteins as well (Patton and Platz, Advanced Drug Delivery Reviews, 8:179-196 (1992)); Timsina et. al., Int. J. Pharm., 101: 1-13 (1995); and Tansey, I. P., Spray Technol. Market, 4:26-29 (1994); French, D. L., Edwards, D. A. and Niven, R. W., Aerosol Sci., 27: 769-783 (1996); Visser, J., Powder Technology 58: 1-10 (1989)); Rudt, S. and R. H. Muller, J. Controlled Release, 22: 263-272 (1992); Tabata, Y, and Y. Ikada, Biomed. Mater. Res., 22: 837-858 (1988); Wall, D. A., Drug Delivery, 2: 10 1-20 1995); Patton, J. and Platz, R., Adv. Drug Del. Rev., 8: 179-196 (1992); Bryon, P., Adv. Drug.

Del. Rev., 5: 107-132 (1990); Patton, J. S., et al., Controlled Release, 28: 15 79-85 (1994); Damms, B. and Bains, W., Nature Biotechnology (1996); Niven, R. W., et al., Pharm. Res., 12(9); 1343-1349 (1995); and Kobayashi, S., et al., Pharm. Res., 13(1): 80-83 (1996), contents of all of which are herein incorporated by reference in their entirety.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments of any of the aspects, the agonist of sFlt1-Hif signalling can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments of any of the aspects, an agonist of sFlt1-Hif signaling (e.g., an sFlt1 polypeptide) is administered to the airway. In some embodiments of any of the aspects, an agonist of sFlt1-Hif signaling (e.g., an sFlt1 polypeptide) is administered intravenously.

In some embodiments of any of the aspects, the agonist of sFlt1-Hif signalling described herein is administered as a monotherapy, e.g., another treatment for the condition described herein, e.g., the lung condition, is not administered to the subject.

In some embodiments of any of the aspects, the methods described herein can further comprise administering a second agent and/or treatment to the subject, e.g. as part of a combinatorial therapy.

In certain embodiments, an effective dose of a composition comprising an agonist of sFlt1-Hif signalling as described herein can be administered to a patient once. In certain embodiments, an effective dose of a composition comprising an agonist of sFlt1-Hif signalling can be administered to a patient repeatedly. For systemic administration, subjects can be administered a therapeutic amount of a composition comprising an agonist of sFlt1-Hif signalling, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments of any of the aspects, an agonist of sFlt1-Hif signaling (e.g., an sFlt1 polypeptide) is administered at a dose of from about 5 mcg polypeptide/kg to about 50 mcg polypeptide/kg. In some embodiments of any of the aspects, an agonist of sFlt1-Hif signaling (e.g., an sFlt1 polypeptide) is administered at a dose of from 5 mcg polypeptide/kg to 50 mcg polypeptide/kg. In some embodiments of any of the aspects, an agonist of sFlt1-Hif signaling (e.g., an sFlt1 polypeptide) is administered at a dose of from about 10 mcg polypeptide/kg to about 40 mcg polypeptide/kg. In some embodiments of any of the aspects, an agonist of sFlt1-Hif signaling (e.g., an sFlt1 polypeptide) is administered at a dose of from 10 mcg polypeptide/kg to 40 mcg polypeptide/kg. In some embodiments of any of the aspects, an agonist of sFlt1-Hif signaling (e.g., an sFlt1 polypeptide) is administered at a dose of about 20 mcg polypeptide/kg.

In some embodiments of any of the aspects, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. VEGF levels and/or at least one measure of lung function by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to the agonist of sFlt1-Hif signalling. The desired dose or amount of activation can be administered at one time or divided into subdoses, e.g., 2-4 subdoses and administered over a period of time, e.g., at appropriate intervals through the day or other appropriate schedule. In some embodiments of any of the aspects, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an agonist of sFlt1-Hif signalling can be administered over a period of time, such as over a 5 minute, 10 minute, 15 minute, 20 minute, or 25 minute period.

The dosage ranges for the administration of an agonist of sFlt1-Hif signalling, according to the methods described herein depend upon, for example, the form of the agonist, its potency, and the extent to which symptoms, markers, or indicators of a condition described herein are desired to be reduced, for example the extent to which, for example, lung growth and/or repair are desired to be induced. The dosage should not be so large as to cause adverse side effects, such as hyperplasia. Generally, the dosage will vary with the age, condition, and sex of the patient and can be determined by one of skill in the art. The dosage can also be adjusted by the individual physician in the event of any complication.

The efficacy of an agonist of sFlt1-Hif signalling in, e.g. the treatment of a condition described herein, or to induce a response as described herein can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. VEGF levels and/or lung function. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. VEGF levels and/or lung function). It is well within the ability of one skilled in the art to monitor efficacy of administration and/or treatment by measuring any one of such parameters, or any combination of parameters. Efficacy can be assessed in animal models of a condition described herein, for example treatment of mouse models of pneumonectomy. When using an experimental animal model, efficacy of treatment is evidenced when a statistically significant change in a marker is observed, e.g. at least one functional measure of lung function described in the examples herein. The efficacy of a given dosage combination can also be assessed in an animal model, e.g. a mouse model of pneumonectomy.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments of any of the aspects, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments of any of the aspects, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments of any of the aspects, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of the conditions described herein. A subject can be male or female.

A subject can be one who has been previously diagnosed with or identified as suffering from or having a condition in need of treatment or one or more complications related to such a condition, and optionally, have already undergone treatment for the condition or the one or more complications related to the condition. Alternatively, a subject can also be one who has not been previously diagnosed as having the condition or one or more complications related to the condition. For example, a subject can be one who exhibits one or more risk factors for the condition or one or more complications related to the condition or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

In the various embodiments described herein, it is further contemplated that variants (naturally occurring or otherwise), alleles, homologs, conservatively modified variants, and/or conservative substitution variants of any of the particular polypeptides described are encompassed. As to amino acid sequences, one of skill will recognize that individual substitutions, deletions or additions to a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid and retains the desired activity of the polypeptide. Such conservatively modified variants are in addition to and do not exclude polymorphic variants, interspecies homologs, and alleles consistent with the disclosure.

Where naturally occurring polypeptides and nucleic acids (or fragments thereof) are described herein, it is contemplated herein that naturally occurring homologs, orthologs, and alleles of the reference polypeptide and/or nucleic acid can be used in alternative embodiments. Sequences of such homologs, orthologs, and alleles are readily obtained by sequence homology searches or querying databases such as that maintained by NCBI.

A given amino acid can be replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. Polypeptides comprising conservative amino acid substitutions can be tested in any one of the assays described herein to confirm that a desired activity, e.g. VEGF-binding activity and specificity of a native or reference polypeptide is retained.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H). Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class. Particular conservative substitutions include, for example; Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

In some embodiments of any of the aspects, the polypeptide described herein (or a nucleic acid encoding such a polypeptide) can be a functional fragment of one of the amino acid sequences described herein. As used herein, a "functional fragment" is a fragment or segment of a peptide which retains at least 50% of the wildtype reference polypeptide's activity according to the assays described below herein. A functional fragment can comprise conservative substitutions of the sequences disclosed herein.

In some embodiments of any of the aspects, the polypeptide described herein can be a variant of a sequence described herein. In some embodiments of any of the aspects, the variant is a conservatively modified variant. Conservative substitution variants can be obtained by mutations of native nucleotide sequences, for example. A "variant," as referred to herein, is a polypeptide substantially homologous to a native or reference polypeptide, but which has an amino acid sequence different from that of the native or reference polypeptide because of one or a plurality of deletions, insertions or substitutions. Variant polypeptide-encoding DNA sequences encompass sequences that comprise one or more additions, deletions, or substitutions of nucleotides when compared to a native or reference DNA sequence, but that encode a variant protein or fragment thereof that retains activity. A wide variety of PCR-based site-specific mutagenesis approaches are known in the art and can be applied by the ordinarily skilled artisan.

A variant amino acid or DNA sequence can be at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTp or BLASTn with default settings).

In some embodiments of any of the aspects described herein, a polypeptide can be a polypeptide with a sequence at least 90%, at least 95%, at least 98%, or at least 99% identical to one of the wild-type reference sequences provided herein (or another known wild-type reference sequence for that relevant gene/protein) which displays the same type of activity as the reference sequence molecule, e.g., VEGF binding activity, lung tissue or repair enchancing activity, etc.

Alterations of the native amino acid sequence can be accomplished by any of a number of techniques known to one of skill in the art. Mutations can be introduced, for example, at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion. Alternatively, oligonucleotide-directed site-specific mutagenesis procedures can be employed to provide an altered nucleotide sequence having particular codons altered according to the substitution, deletion, or insertion required. Techniques for making such alterations are very well established and include, for example, those disclosed by Walder et al. (Gene 42:133, 1986); Bauer et al. (Gene 37:73, 1985); Craik (BioTechniques, Jan. 1985, 12-19); Smith et al. (Genetic Engineering: Principles and Methods, Plenum Press, 1981); and U.S. Pat. Nos. 4,518,584 and 4,737,462, which are herein incorporated by reference in their entireties. Any cysteine residue not involved in maintaining the proper conformation of the polypeptide also can be substituted, generally with serine, to improve the oxidative stability of the molecule and prevent aberrant crosslinking. Conversely, cysteine bond(s) can be added to the polypeptide to improve its stability or facilitate oligomerization.

The polypeptides described herein can be further modified to provide means to increase or improve targeting, e.g., linked with a molecular counter-ligand, for example but not limited to, molecules which target the lung epithelium, to make the polypeptide tissue specific.

In one embodiment, the polypeptide is linked to a carrier to enhance its bioavailability. Such carriers are known in the art and include poly (alkyl) glycol such as poly ethylene glycol (PEG) or methoxypolyethylene glycol (mPEG) which can increase the in vivo half life of proteins to which they are conjugated. Methods of PEGylation of a peptide are well known by one of ordinary skill in the art, and are considerations of, for example, how large a PEG polymer to use. In some embodiments of any of the aspects, a peptide can be fused to serum albumin to increase the serum half-life of therapeutic polypeptides and peptides.

In some embodiments the polypeptide described herein can be conjugated to a second entity, for example, to promote stability or for specific cell type targeting. In some embodiments of any of the aspects, a polypeptide or fragments, derivatives or variants thereof can be conjugated to a first fusion partner (i.e. IgG1 Fc). The conjugation can be a non-covalent or covalent interaction, for example, by means of chemical crosslinkage or conjugation. As discussed herein, In some embodiments of any of the aspects, the polypeptide is fused to serum albumin to increase the serum half-life of the polypeptide.

In some embodiments of any of the aspects, the polypeptide can also be fused to a second fusion partner, for example, to a polypeptide that targets the product to a desired location, or, for example, a tag that facilitates its purification, if so desired. Tags and fusion partners can be designed to be cleavable, if so desired. Another modification specifically contemplated is attachment, e.g., covalent attachment, to a polymer. In one aspect, polymers such as polyethylene glycol (PEG) or methoxypolyethylene glycol (mPEG) can increase the in vivo half-life of proteins to which they are conjugated. Methods of PEGylation of polypeptide agents are well known to those skilled in the art, as are considerations of, for example, how large a PEG polymer to use.

As used herein, the term "conjugate" or "conjugation" refers to the attachment of two or more entities to form one entity. For example, the methods of the present invention provide conjugation of a peptide or fragments, derivatives or variants thereof joined with another entity, for example a moiety such as a first fusion partner that makes the polypeptide stable, such as Ig carrier particle, for example IgG1 Fc. The attachment can be by means of linkers, chemical modification, peptide linkers, chemical linkers, covalent or non-covalent bonds, or protein fusion or by any means known to one skilled in the art. The joining can be permanent or reversible. In some embodiments of any of the aspects, several linkers can be included in order to take advantage of desired properties of each linker and each protein in the conjugate. Flexible linkers and linkers that increase the solubility of the conjugates are contemplated for use alone or with other linkers as disclosed herein. Peptide linkers can be linked by expressing DNA encoding the linker to one or more proteins in the conjugate. Linkers can be acid cleavable, photocleavable and heat sensitive linkers. Methods for conjugation are well known by persons skilled in the art and are encompassed for use in the present invention. According to the present invention, the polypeptide or fragments, derivatives or variants thereof, can be linked to the first fusion partner via any suitable means, as known in the art, see for example U.S. Pat. Nos. 4,625,014, 5,057,301 and 5, 514,363, which are incorporated herein in their entirety by reference. For example, the polypeptide e can be covalently conjugated to the IgG1 Fc, either directly or through one or more linkers. In one embodiment, a polypeptide as disclosed herein is conjugated directly to the first fusion partner (e.g. Fc), and in an alternative embodiment, a polypeptide as disclosed herein can be conjugated to a first fusion partner (such as IgG1 Fc) via a linker, e.g. a transport enhancing linker.

A large variety of methods for conjugation of a polypeptide as disclosed herein with a first fusion partner (e.g. Fc) are known in the art. Such methods are e.g. described by Hermanson (1996, Bioconjugate Techniques, Academic Press), in U.S. Pat. Nos. 6,180,084 and 6,264,914 which are incorporated herein in their entirety by reference and include e.g. methods used to link haptens to carriers proteins as routinely used in applied immunology (see Harlow and Lane, 1988, "Antibodies: A laboratory manual", Cold Spring Harbor Laboratory Press, Cold Spring Harbor, NY). It is recognized that, in some cases, a polypeptide can lose efficacy or functionality upon conjugation depending, e.g., on the conjugation procedure or the chemical group utilized therein. However, given the large variety of methods for conjugation the skilled person is able to find a conjugation method that does not or least affects the efficacy or functionality of the entities, such as the polypeptide to be conjugated. Suitable methods for conjugation of a polypeptide as disclosed herein with a first fusion partner (e.g. Fc) include e.g. carbodimide conjugation (Bauminger and Wilchek, 1980, Meth. Enzymol. 70: 151-159). Alternatively, a moiety can be coupled to a targeting agent as described by Nagy et al., Proc. Natl. Acad. Sci. USA 93:7269-7273 (1996), and Nagy et al., Proc. Natl. Acad. Sci. USA 95:1794-1799 (1998), each of which are incorporated herein by reference. Another method for conjugating one can use is, for example sodium periodate oxidation followed by reductive alkylation of appropriate reactants and glutaraldehyde crosslinking.

One can use a variety of different linkers to conjugate a polypeptide as disclosed herein with a first fusion partner (e.g. Fc), for example but not limited to aminocaproic horse radish peroxidase (HRP) or a heterobiofunctional cross-linker, e.g. carbonyl reactive and sulfhydryl-reactive cross-linker. Heterobiofunctional cross linking reagents usually contain two reactive groups that can be coupled to two different function targets on proteins and other macromolecules in a two or three-step process, which can limit the degree of polymerization often associated with using homo-biofunctional cross-linkers. Such multi-step protocols can offer a great control of conjugate size and the molar ratio of components. The term "linker" refers to any means to join two or more entities, for example a polypeptide as disclosed herein with a first fusion partner (e.g. Fc). A linker can be a covalent linker or a non-covalent linker. Examples of covalent linkers include covalent bonds or a linker moiety covalently attached to one or more of the proteins to be linked. The linker can also be a non-covalent bond, e.g. an organometallic bond through a metal center such as platinum atom. For covalent linkages, various functionalities can be used, such as amide groups, including carbonic acid derivatives, ethers, esters, including organic and inorganic esters, amino, urethane, urea and the like. To provide for linking, the effector molecule and/or the probe can be modified by oxidation, hydroxylation, substitution, reduction etc. to provide a site for coupling. It will be appreciated that modification which do not significantly decrease the function of the polypeptide as disclosed herein or the first fusion partner (e.g. Fc) are preferred.

In some embodiments of any of the aspects, a polypeptide described herein can be modified to comprise one or more amino acids other than the 20 amino acids commonly referred to as the 20 naturally occurring amino acids.

In some embodiments of any of the aspects, any of the amino acids of a polypeptide described herein, including the terminal amino acids, can be modified either by natural processes such as glycosylation and other post-translational modifications, or by chemical modification techniques which are well known in the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which can be present in polypeptides of the present invention are, to name an illustrative few, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance, 1. E. Creighton, Proteins-Structure and Molecular Properties, 2nd Ed., W.H. Freeman and Company, New York, 1993. Many detailed reviews are available on this subject, such as, for example, those provided by Wold, F., in Posttranslational Covalent Modification of Proteins, B. C. Johnson, Ed., Academic Press, New York, pp 1-12, 1983; Sifter et al., Meth. Enzymol. 182: 626-646, 1990 and Rattan et al., Protein Synthesis: Posttranslational Modifications and Aging, Ann. N.Y. Acad. Sci. 663: 48-62, 1992.

In some embodiments of any of the aspects, N-methyl and hydroxy-amino acids can be substituted for conventional amino acids in solid phase peptide synthesis. However, production of polymers with reduced peptide bonds requires synthesis of the dimmer of amino acids containing the reduced peptide bond. Such dimers are incorporated into polymers using standard solid phase synthesis procedures. Other synthesis procedures are well known in the art.

Accordingly, functional derivatives of the polypeptides described herein may be prepared by modification of the amino acids of polypeptide are encompassed for use in the methods and compositions as disclosed herein. Modifications may occur anywhere in the polypeptide sequence or its functional derivative polypeptide, including the peptide backbone, the amino acid side-chains and the amino or carboxyl termini. Modifications may include, for example, acetylation, acylation, ADP-ribosylation, amidation, covalent attachment of other functional moiety, covalent attachment of a lipid or lipid derivative, covalent attachment of phosphotidylinositol, cross-linking, cyclization, disulfide bond formation, demethylation, formation of covalent cross-links, formylation, gamma-carboxylation, glycosylation, glycophosphatidylinositol (GPI) anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. See, for instance, E. Creighton Proteins-Structure and Molecular Properties, 2nd Ed., W. H. Freeman and Company, New York (1993); B. C. Johnson, Post Translational Covalent Modification of Proteins, Academic Press, New York, (1983); Seifter et al., Meth. Enzymol. 182: 626-646 (1990); Rattan et al., Ann. N. Y. Acad. Sci. 663: 48-62 (1992). Preparation of these modified derivatives may, for example, be useful if direct administration of the polypeptide is contemplated.

It will also be appreciated, as is well known and as noted above, that peptides and polypeptides are not always entirely linear. For instance, polypeptides can be branched as a result of ubiquitination, and they can be circular, with or without branching, generally as a result of posttranslational events, including natural processing events and events brought about by human manipulation which do not occur naturally.

Circular, branched and branched circular polypeptides can be synthesized by non translational natural processes and by entirely synthetic methods.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and; synthetic polypeptides and such modifications can be present in polypeptides of the present invention, as well. For instance, the amino terminal residue of polypeptides made in E. coli, prior to proteolytic processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylation host, generally a eukaryotic cell. Insect cells often carry out the same post-translational glycosylation as mammalian cells and, for this reason, insect cell expression systems have been developed to efficiently express mammalian proteins having native patterns of glycosylation, inter alia. Similar considerations apply to other modifications.

In some embodiments of any of the aspects, a polypeptide described herein (e.g., an sFlt1 polypeptide) is a polypeptide produced in a non-endogenous host, e.g., a bacterial cell, yeast cell, or insect cell.

It will be appreciated that the same type of modification can be present to the same or varying degree at several sites in a given polypeptide. Also, a given peptide or polypeptide can contain many types of modifications.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

In some embodiments of any of the aspects, a nucleic acid encoding an agonist of sFlt1-Hif signalling can be a DNA or mRNA. In some embodiments of any of the aspects, a nucleic acid encoding an agonist of sFlt1-Hif signalling can be a modified DNA or mRNA, e.g., chemically modified to enhance stability or other beneficial characteristics. The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages.

In some embodiments of any of the aspects, a nucleic acid encoding a polypeptide as described herein (e.g. an sFlt1 polypeptide) is comprised by a vector. In some of the aspects described herein, a nucleic acid sequence encoding a given polypeptide as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, In some embodiments of any of the aspects, be combined with other suitable compositions and therapies. In some embodiments of any of the aspects, the vector is episomal. The use of a suitable episomal vector provides a means of maintaining the nucleotide of interest in the subject in high copy number extra chromosomal DNA thereby eliminating potential effects of chromosomal integration.

In some embodiments of any of the aspects, a nucleic acid encoding a polypeptide described herein, e.g., an sFlt1 polypeptide, is operably linked to a non-endogenous promoter (e.g., a non-human promoter).

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments of any of the aspects, a pharmaceutically acceptable carrier can be a carrier other than water. In some embodiments of any of the aspects, a pharmaceutically acceptable carrier can be a cream, emulsion, gel, liposome, nanoparticle, and/or ointment. In some embodiments of any of the aspects, a pharmaceutically acceptable carrier can be an artificial or engineered carrier, e.g., a carrier that the active ingredient would not be found to occur in nature.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, $4^{th}$ ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of inducing growth and/or repair of lung tissue, the method comprising contacting the lung tissue with an agonist of sFlt1-Hif signalling.

2. A method of inducing growth and/or repair of lung tissue in a subject in need thereof, the method comprising administering a therapeutically effective amount of an agonist of sFlt1-Hif signalling to the subject.

3. The method of paragraph 2, wherein the growth and/or repair of lung tissue is compensatory lung growth.

4. The method of any of paragraphs 2-3, wherein the subject is a subject with severe pulmonary hypoplasia; hypoplastic lung disease; congenital diaphragmatic hernia; bronchopulmonary dysplasia; emphysema; a disease with deficient alveolar count; alveolar capillary dysplasia; or who has undergone a pneumonectomy.

5. The method of any of paragraphs 2-4, wherein the subject is not diagnosed with or in need of treatment for an inflammatory condition.

6. The method of any of paragraphs 1-5, wherein the agonist of sFlt1-Hif signaling is sFlt1 polypeptide.

7. The method of paragraph 6, wherein the sFlt1 polypeptide is a polypeptide comprising the sequence of one of SEQ ID NOs: 2-13.

8. The method of paragraph 6, wherein the sFlt1 polypeptide is a polypeptide comprising a sequence at least 95% identical to the sequence of one of SEQ ID NOs: 2-13 and retaining the activity of a polypeptide of SEQ ID NOs: 2-13.

9. The method of any of paragraphs 6-8, wherein the agonist further comprises an Fc domain conjugated to the sFlt1 polypeptide.

10. The method of any of paragraphs 6-9, wherein the agonist is administered to the airway.

11. The method of any of paragraphs 6-9 wherein the agonist is administered intravenously.

12. The method of any of paragraphs 6-9, wherein the agonist is administered topically.

13. The method of any of paragraphs 6-12, wherein the agonist is administered at a dose of from about 5 mcg/kg to about 50 mcg/kg.

14. The method of any of paragraphs 6-12, wherein the agonist is administered at a dose of about 20 mcg/kg.

15. The method of any of paragraphs 1-5, wherein the agonist of sFlt1-Hif signaling is an agonist of HIF1σ; HIF1β; and/or HIF2σ.

16. The method of paragraph 15, wherein the agonist is a HIF1σ; HIF1β; and/or HIF2σ polypeptide and/or a nucleic acid encoding said polypeptide.

17. The method of paragraph 15, wherein the agonist is a HIF Prolyl hydroxylase antagonist.

18. The method of paragraph 17, wherein the HIF Prolyl hydroxylase antagonist is JTZ-951; FG-4592; GSK1278863; FG-4592; or MK-8617.

19. The method of any of paragraphs 1-18, whereby endogenous VEGF levels are increased in the lung tissue and/or subject.

20. The method of any of paragraphs 1-19, wherein the method results in higher lung volume, increased inspiratory capacity, increased exercise capacity, and/or increased pulmonary compliance.

EXAMPLES

Example 1

C57B16 mice were randomized to receive daily intraperitoneal injection of either saline or soluble fms-like tyrosine kinase 1 (sFlt1) at a dose of 20 mcg/kg following left pneumonectomy. On post-operative day 4, mice underwent pulmonary function studies and were subsequently euthanized for lung volume measurement. Lung volume was determined by water displacement method. Mice that received sFlt1 treatment showed significantly higher lung volume ($p<0.01$), inspiratory capacity ($p=0.01$), as well as improved pulmonary elastance ($p=0.04$) and compliance ($p=0.04$) (FIGS. 1-4). This therapy can potentially improve lung growth and pulmonary functions in patients suffering from severe pulmonary hypoplasia.

The soluble VEGF receptor binds (sFlt1) VEGF and depletes the circulating VEGF molecule. This sFlt1 molecule has been shown to inhibit tumors and liver regeneration. However, the unexpected finding is that the soluble VEGF receptor accelerated compensatory lung growth after pneumonectomy. This is of interest in children with hypoplastic lung disease such as that in congenital diaphragmatic hernia.

Figure 6:
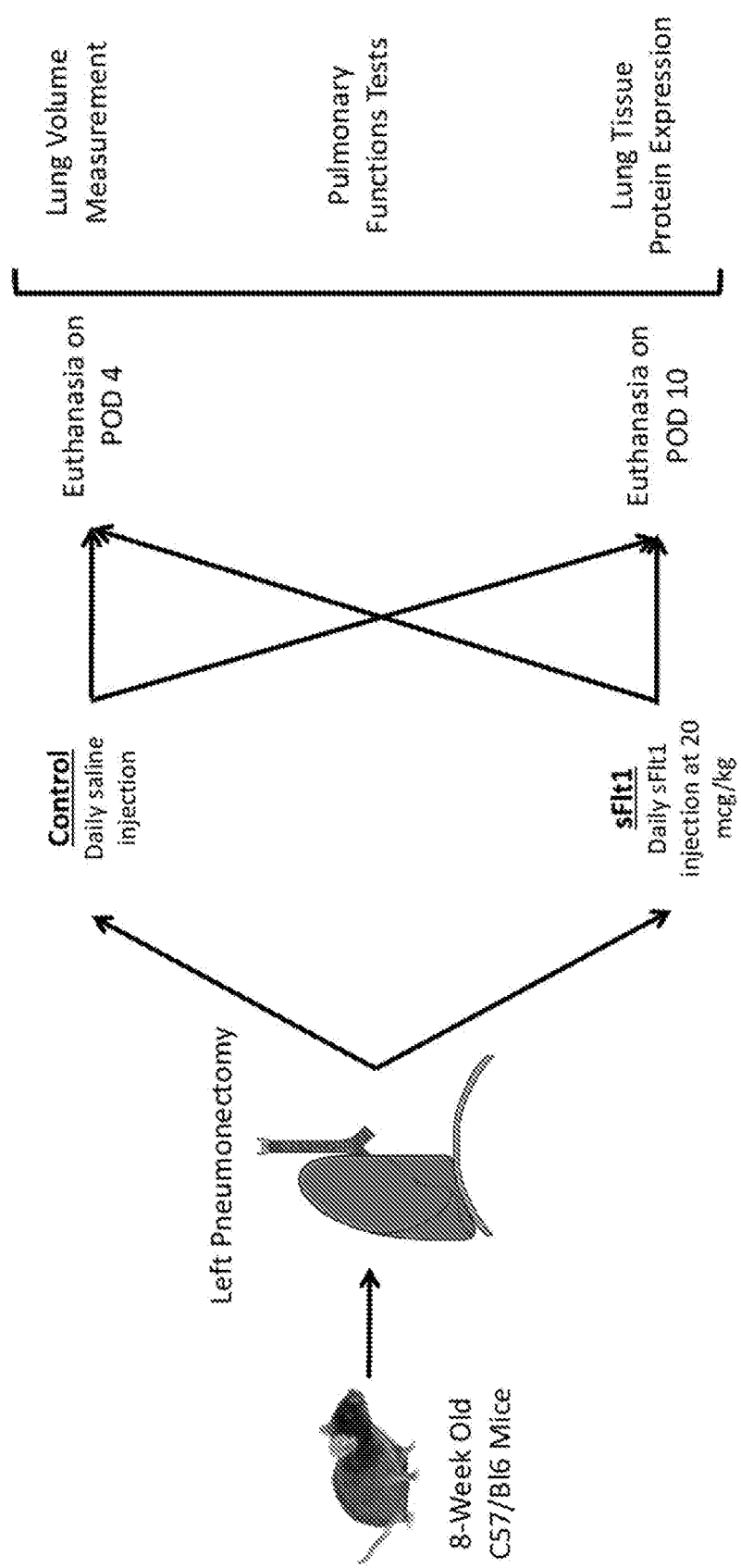
FIG. 6 depicts a schematic of the experimental design.
Figure 7:
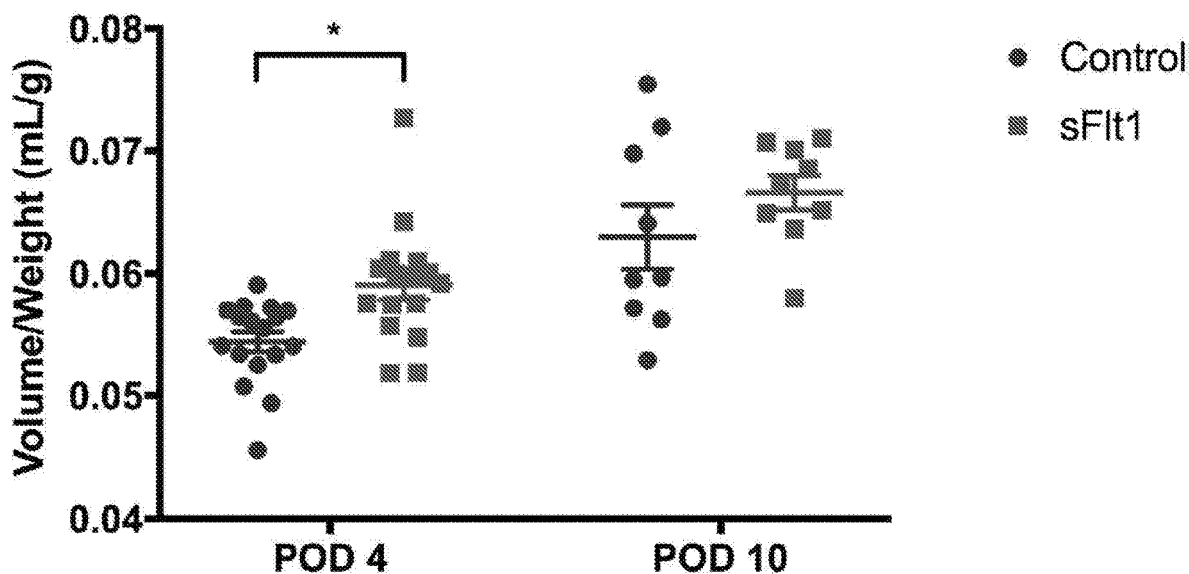
FIG. 7 depicts a graph demonstrating that sFlt1 administration accelerated lung growth.
Figure 8:
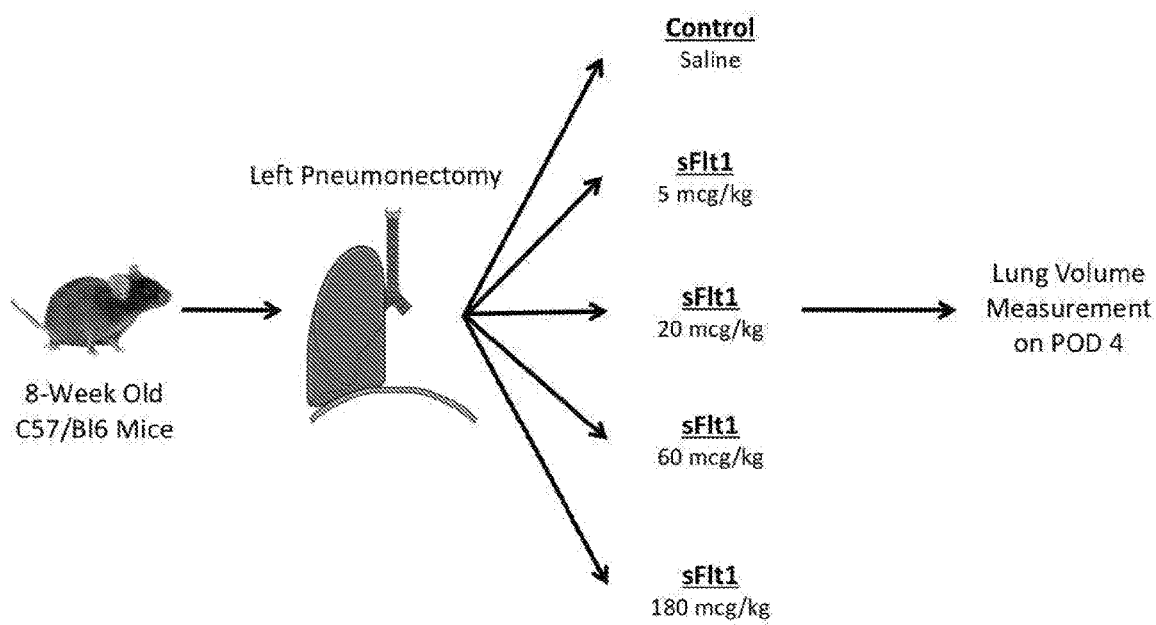
FIG. 8 depicts a schematic of dose response experiments.
Figure 9:
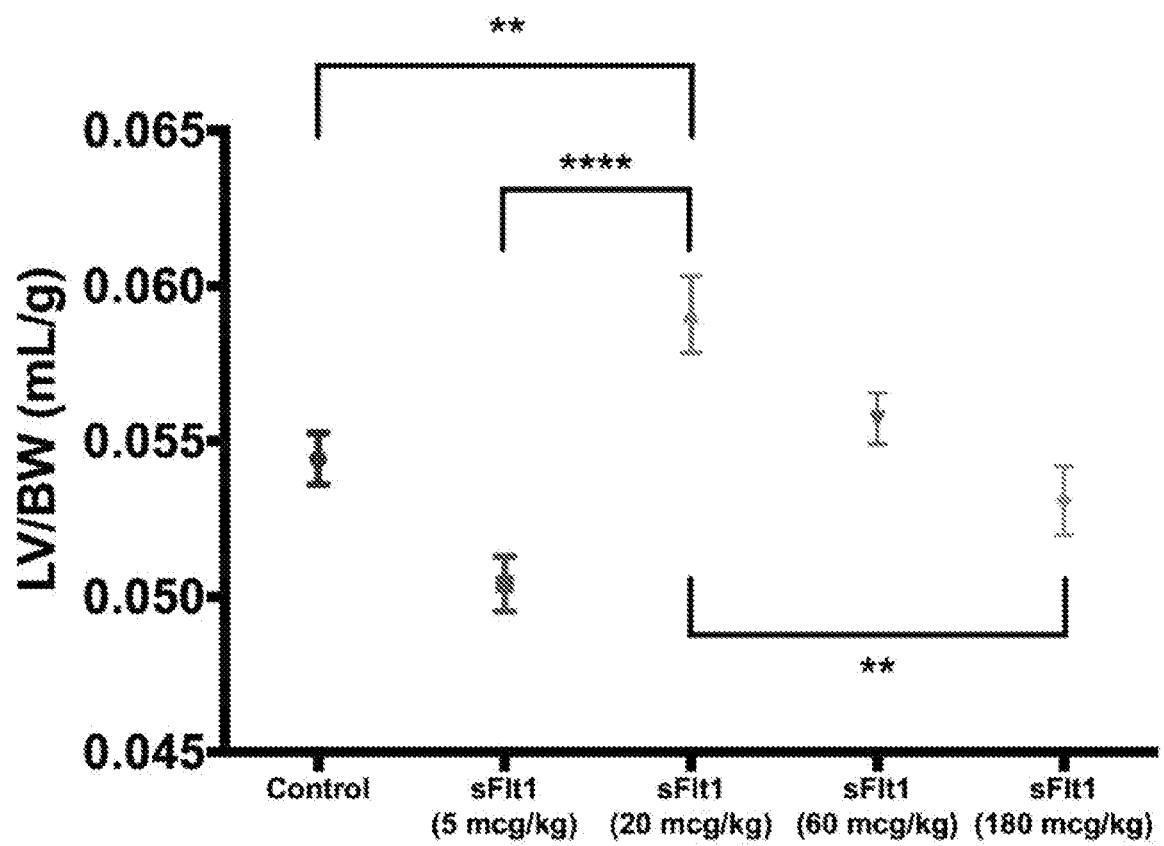
FIG. 9 depicts a graph of sFlt1 dose responses.
Figure 10:
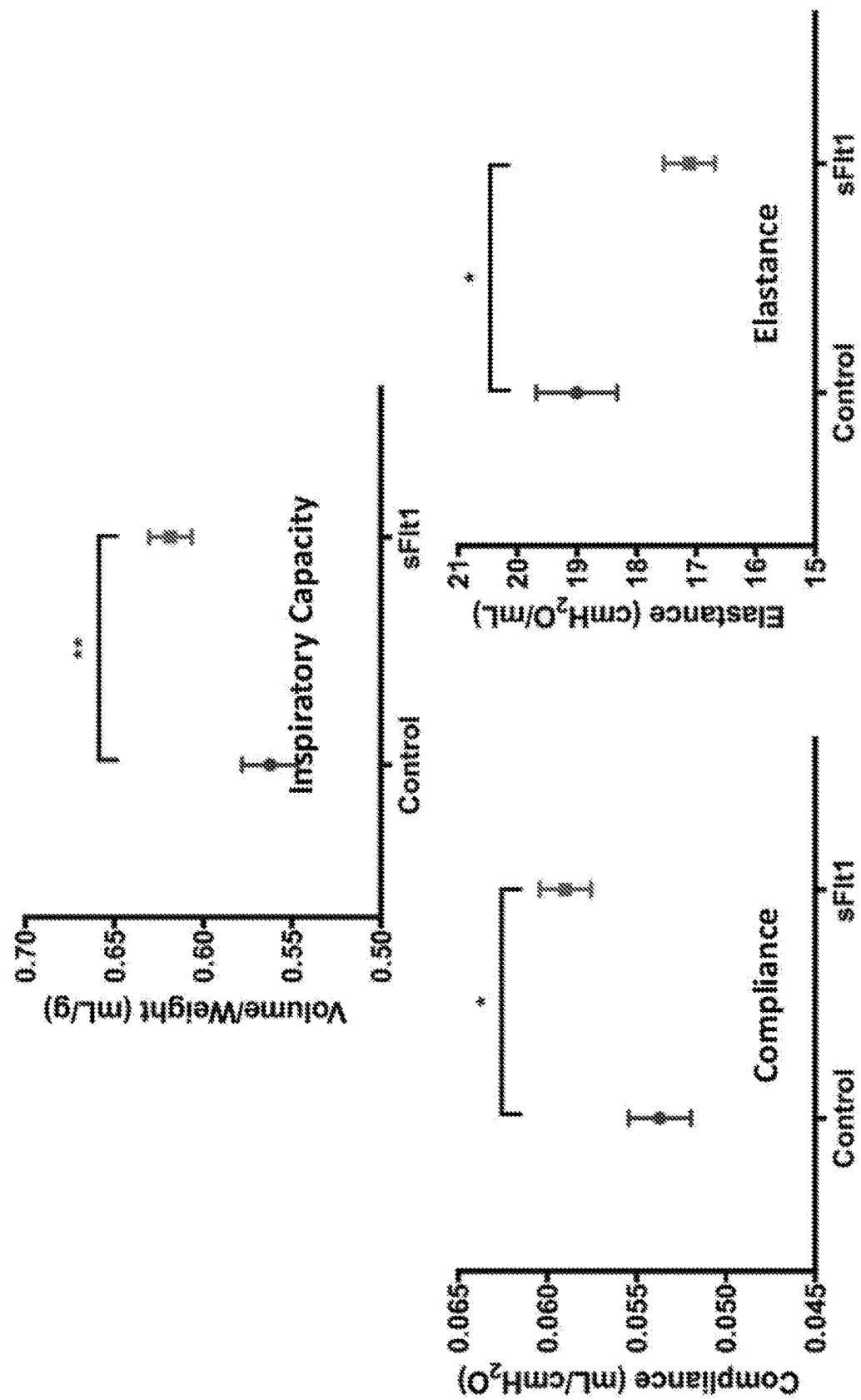
FIG. 10 depicts graphs demonstrating that administration of sFlt1 at 20 mcg/kg improved pulmonary mechanics.

Example 2 sFlt1 was administered to mice according to the experimental design depicted in FIG. 6. The results demonstrate that sFlt1 administration, contrary to expectations, increases lung growth (FIG. 10). The dose response to sFlt1 was investigated (FIG. 8) and, in mice, 20 mcg/kg sFlt1 was the optimal dosing regimen (FIG. 9). Administration of sFlt1 was also demonstrated to improve pulmonary compliance and inspiratory capacity, which accords with the lung volume data (FIG. 10).

Figure 11:
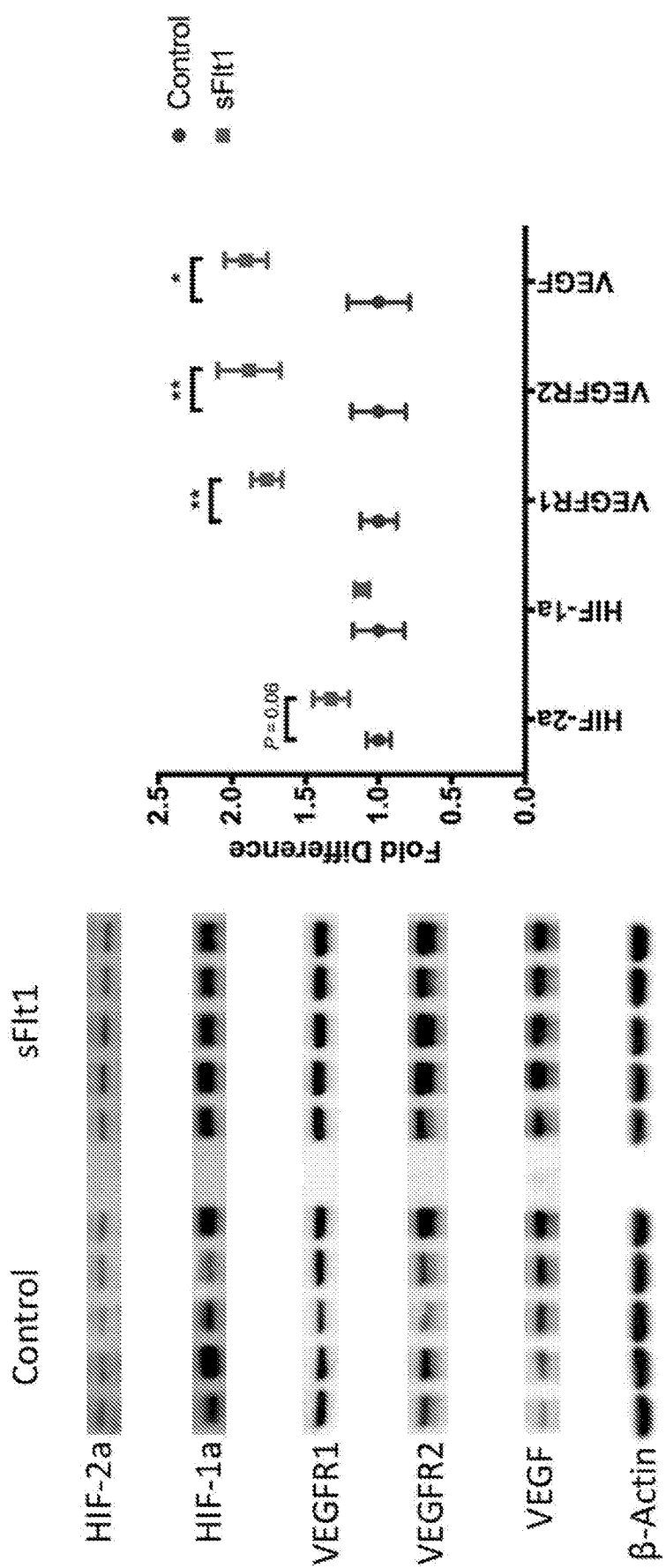
FIG. 11 demonstrates that sFlt1 administration unexpectedly increases the levels of both VEGF and HIF-2α
Figure 12:
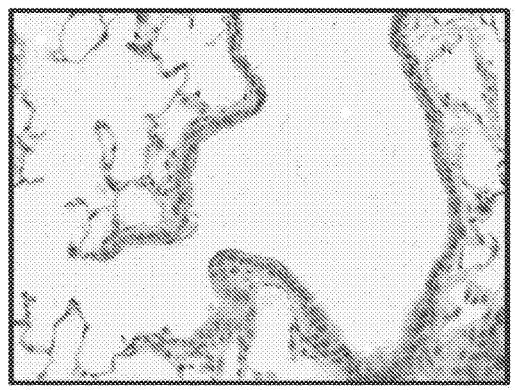
FIG. 12 depicts immunohistochemical measurements of HIF-2α levels.
Figure 12:
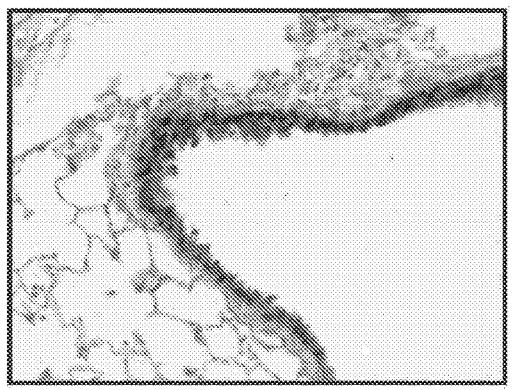
Figure 12:
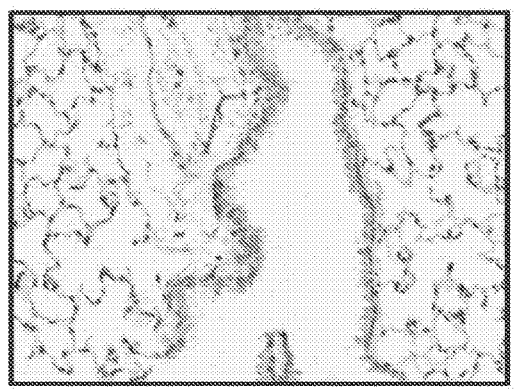
Figure 12:
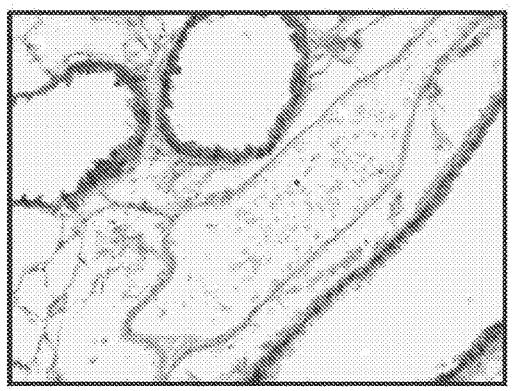
Figure 13:
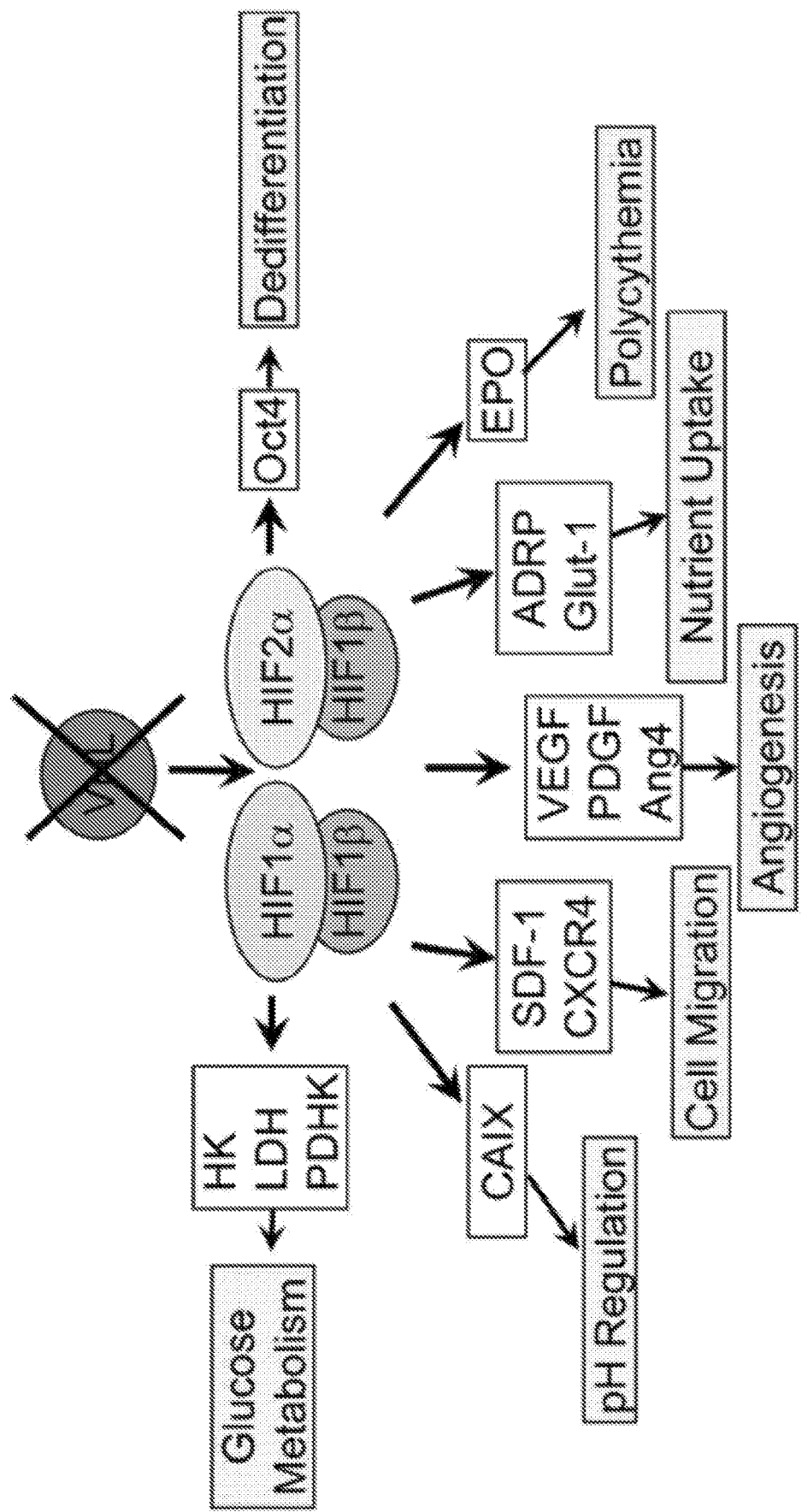
FIG. 13 depicts a diagram of hypoxia-induced factor signaling
Figure 14:
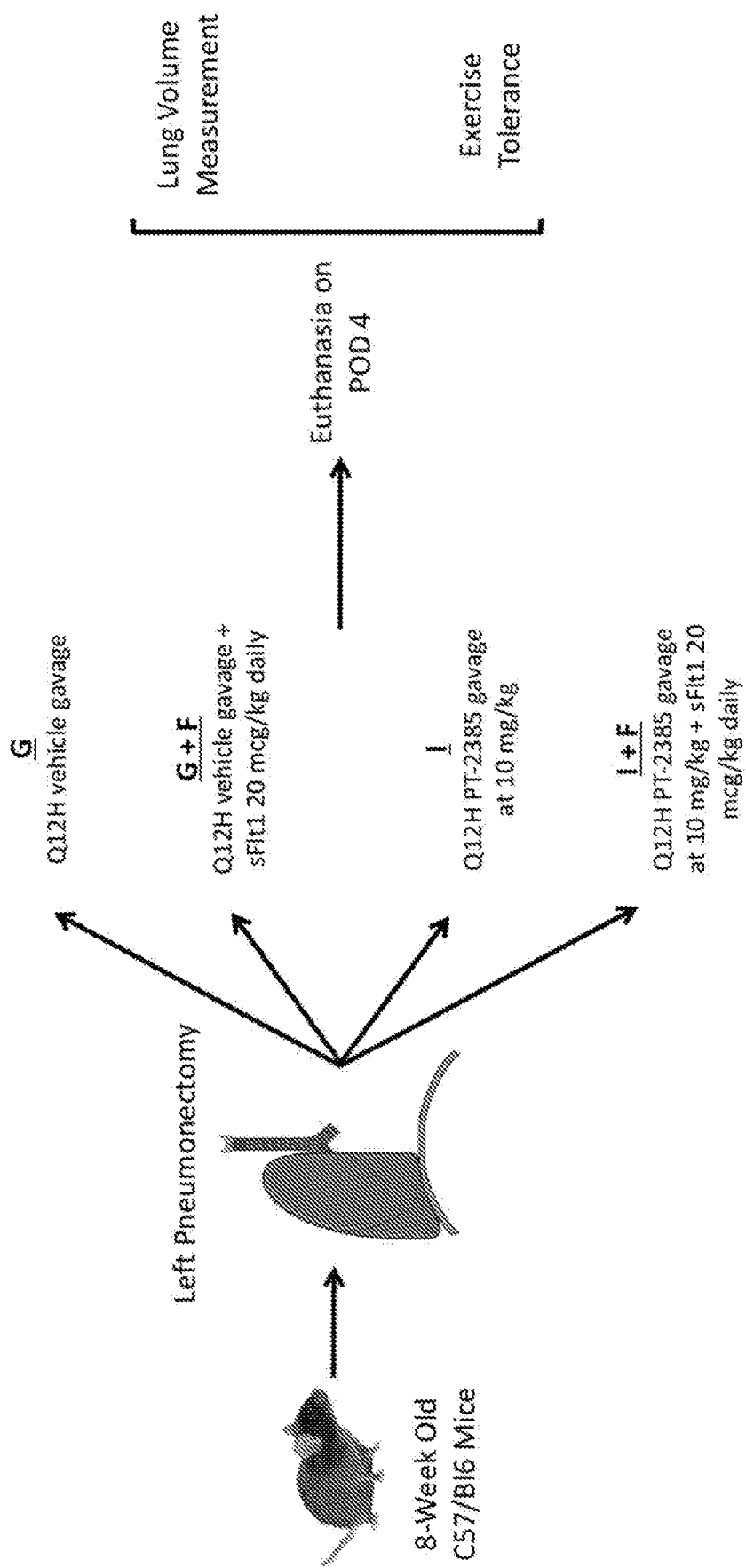
FIG. 14 depicts a diagram of experiments investigating the effect of the HIF-2α inhibitor PT-2385.
Figure 15:
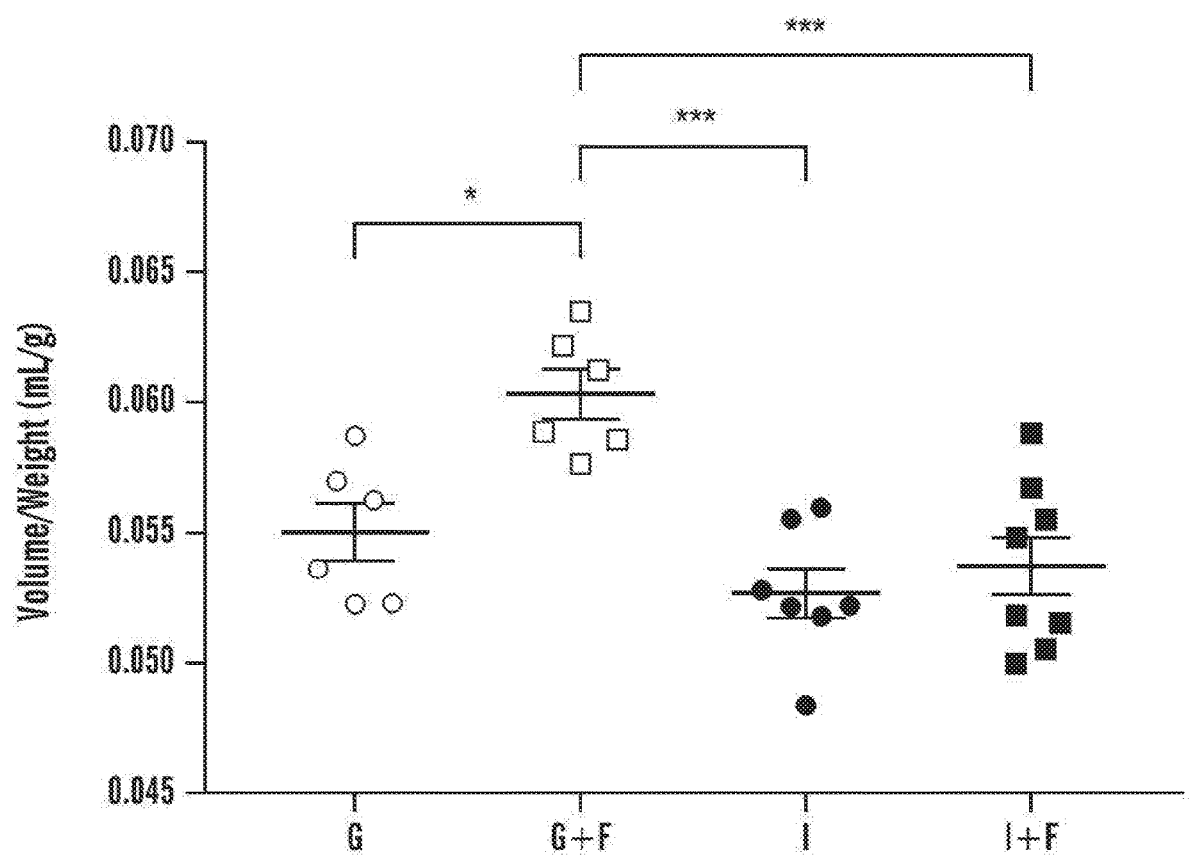
FIG. 15 depicts a graph demonstrating that HIF-2α inhibition blunted the effect of sFlt1.
Figure 16:
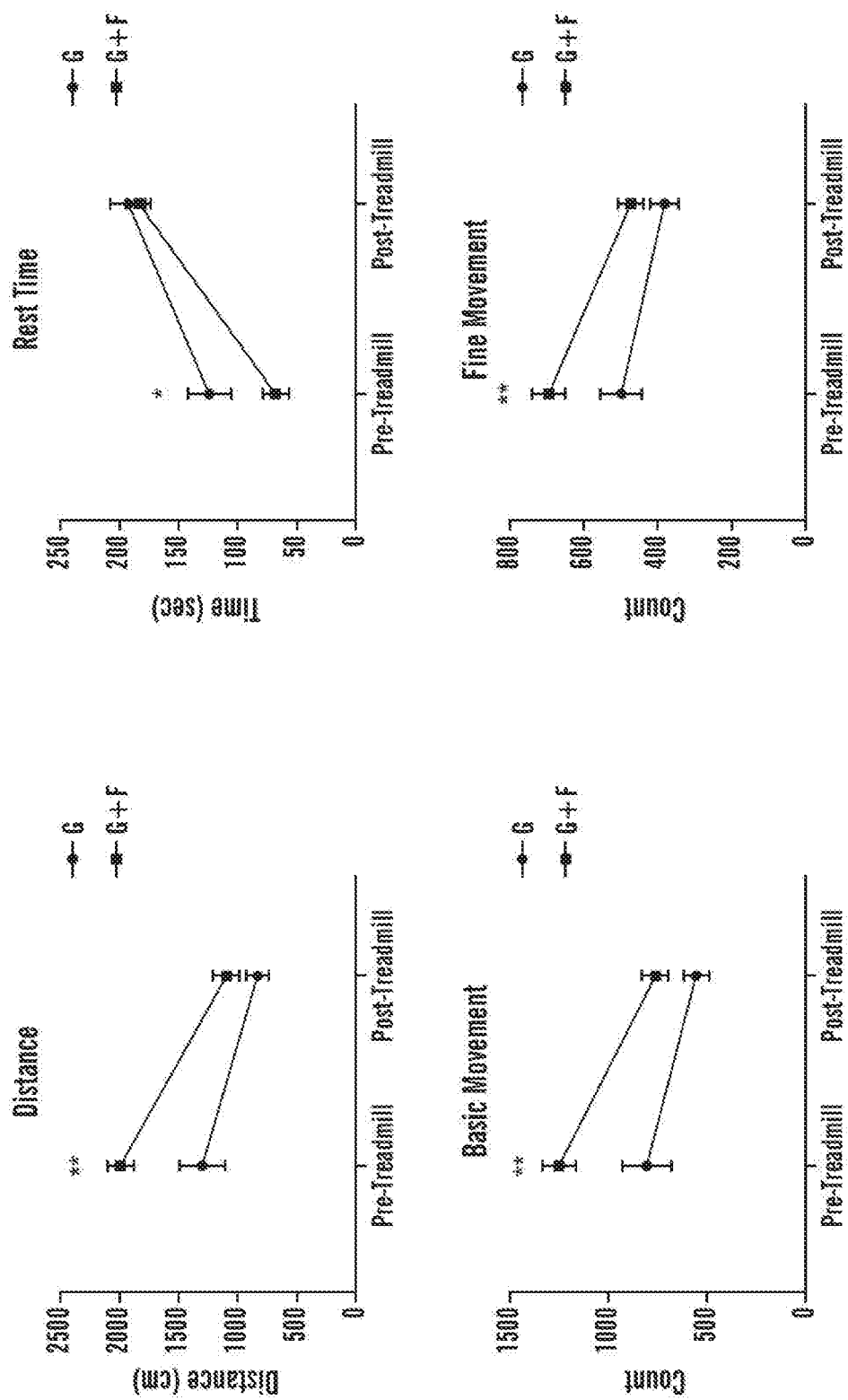
FIG. 16 depicts graphs demonstrating that sFlt1 administration increased baseline activity in exercise tolerance tests.
Figure 17:
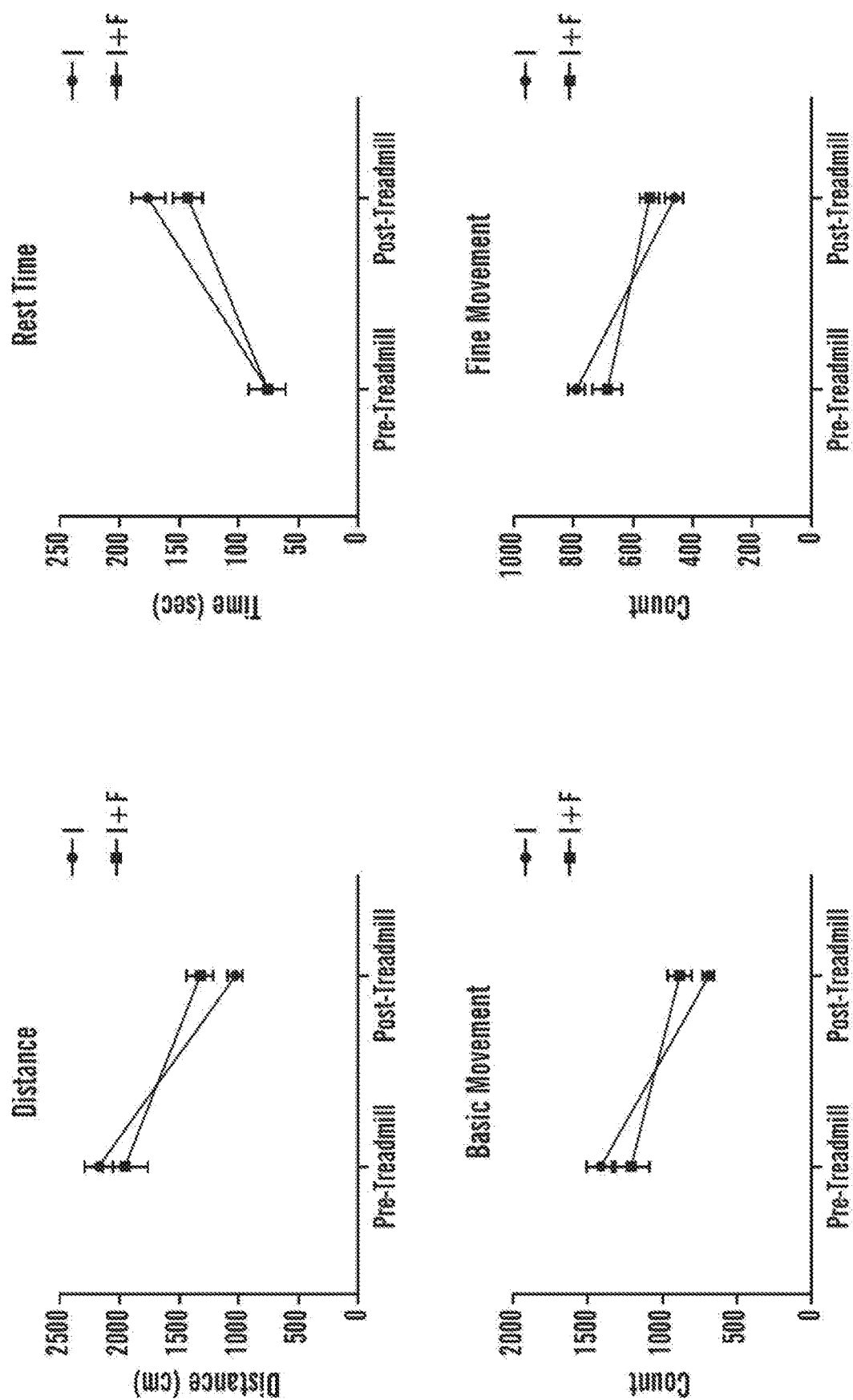
FIG. 17 depicts graphs demonstrating that HIF-2α inhibition blunted the effect of sFlt1 administration on baseline activity in exercise tolerance tests.

Further investigation revealed that sFlt1 administration unexpectedly increases the levels of both VEGF and HIF-2α (FIG. 11, 12) which indicates that sFlt1 increased endogenous production of VEGF by upregulating HIF-2a. The effects of HIF-2α inhibitor PT-2385 on sFlt1 administration were determined (FIG. 14) and inhibition of HIF-2α was shown to blunt the effects of sFlt1 on lung growth (FIG. 15) as well as on the exercise tolerance of the subjects (FIG. 16, 17).

Example 3

Mice underwent 70% partial hepatectomy and were randomized to receive saline (control) or one of 3 doses of Flt1 (10, 20, or 50 ug/kg) via intraperitoneal injection. Treatment was performed daily and mice were euthanized on post-operative day (POD) 4 for organ harvest. Liver samples were weighed and normalized against body weight. Comparison of normalized liver weight among the 4 experimental groups was achieved with analysis of variance (ANOVA). On POD 4, there was no difference in liver weight among the experimental groups.

What is claimed is:

1. A method of inducing growth and/or repair of lung tissue in a subject in need thereof, the method comprising administering a therapeutically effective amount of an agonist of soluble Feline McDonough Sarcoma (FMS) like tyrosine kinase 1 (sFlt1)-hypoxia inducible factor 1 (Hif) signalling to the subject,
wherein the agonist of sFlt1-Hif signalling is a Hif prolyl hydroxylase antagonist selected from JTZ-951, FG-4592, GSK1278863, and MK-8617:
wherein the subject has severe pulmonary hypoplasia, hypoplastic lung disease, congenital diaphragmatic hernia, a disease with deficient alveolar count, alveolar capillary dysplasia, or has undergone a pneumonectomy, and
wherein the subject is not diagnosed with or in need of treatment for an inflammatory condition.

2. The method of claim 1, wherein the growth and/or repair of lung tissue is compensatory lung growth.

3. The method of claim 1, wherein the agonist of sFlt1-Hif signalling is administered to the airway.

4. The method of claim 1, wherein the agonist of sFlt1-Hif signalling is administered intravenously.

5. The method of claim 1, wherein the agonist of sFlt1-Hif signalling is administered topically.

6. The method of claim 1, wherein the agonist of sFlt1-Hif signalling is administered at a dose of from 5 mcg/kg to 50 mcg/kg.

7. The method of claim 6, wherein the agonist of sFlt1-Hif signalling is administered at a dose of 20 mcg/kg.

8. The method of claim 1, whereby endogenous vascular endothelial growth factor (VEGF) levels increase in the lung tissue of the subject.

9. The method of claim 1, wherein the method results in a higher lung volume, an increase in inspiratory capacity, an increase in exercise capacity, and/or an increase in pulmonary compliance.

10. A method of inducing growth and/or repair of lung tissue in a subject in need thereof, the method comprising administering a therapeutically effective amount of FG-4592, wherein the subject is not diagnosed with or in need of treatment for an inflammatory condition.

11. The method of claim 10, wherein the subject has severe pulmonary hypoplasia, hypoplastic lung disease, congenital diaphragmatic hernia, a disease with deficient alveolar count, alveolar capillary dysplasia, or has undergone a pneumonectomy.

12. The method of claim 10, wherein the FG-4592 is administered to the airway.

13. The method of claim 10, wherein the FG-4592 is administered intravenously.

14. The method of claim 10, wherein the FG-4592 is administered topically.

15. The method of claim 10, whereby endogenous vascular endothelial growth factor (VEGF) levels increase in the lung tissue of the subject.

16. The method of claim 10, wherein the method results in a higher lung volume, an increase in inspiratory capacity, an increase in exercise capacity, and/or an increase in pulmonary compliance.

17. A method of inducing compensatory lung growth in a subject in need thereof, the method comprising administering a therapeutically effective amount of an agonist of soluble Feline McDonough Sarcoma (FMS) like tyrosine kinase 1 (sFlt1)-hypoxia inducible factor 1 (Hif) signalling to the subject,
wherein the agonist of sFlt1-Hif signalling is a Hif prolyl hydroxylase antagonist selected from JTZ-951, FG-4592, GSK1278863, and MK-8617.

18. The method of claim 17, wherein the subject has severe pulmonary hypoplasia, hypoplastic lung disease, congenital diaphragmatic hernia, emphysema, a disease with deficient alveolar count, alveolar capillary dysplasia, or has undergone a pneumonectomy.

19. The method of claim 17, wherein the agonist of sFlt1-Hif signalling is administered to the airway.

20. The method of claim 17, wherein the agonist of sFlt1-Hif signalling is administered intravenously.

21. The method of claim 17, wherein the agonist of sFlt1-Hif signalling is administered topically.

22. The method of claim 17, wherein the agonist of sFlt1-Hif signalling is administered at a dose of from 5 mcg/kg to 50 mcg/kg.

23. The method of claim 22, wherein the agonist of sFlt1-Hif signalling is administered at a dose of 20 mcg/kg.

24. The method of claim 17, whereby endogenous vascular endothelial growth factor (VEGF) levels increase in the lung tissue of the subject.

25. The method of claim 17, wherein the method results in a higher lung volume, an increase in inspiratory capacity, an increase in exercise capacity, and/or an increase in pulmonary compliance.

26. A method of inducing compensatory lung growth in a subject in need thereof, the method comprising administering a therapeutically effective amount of FG-4592.

27. The method of claim 26, wherein the subject has severe pulmonary hypoplasia, hypoplastic lung disease, congenital diaphragmatic hernia, emphysema, a disease with deficient alveolar count, alveolar capillary dysplasia, or has undergone a pneumonectomy.

28. The method of claim 26, wherein the FG-4592 is administered to the airway.

29. The method of claim 26, wherein the FG-4592 is administered intravenously.

30. The method of claim 26, wherein the FG-4592 is administered topically.

31. The method of claim 26, whereby endogenous vascular endothelial growth factor (VEGF) levels increase in the lung tissue of the subject.

32. The method of claim 26, wherein the method results in a higher lung volume, an increase in inspiratory capacity, an increase in exercise capacity, and/or an increase in pulmonary compliance.

* * * * *